(12) United States Patent
Miguel et al.

(10) Patent No.: US 10,548,924 B2
(45) Date of Patent: Feb. 4, 2020

(54) USE OF ADIPOSE TISSUE-DERIVED STROMAL STEM CELLS IN TREATING FISTULA

(71) Applicants: Universidad Autonoma de Madrid, Madrid (ES); TIGENIX, S.A.U., Madrid (ES)

(72) Inventors: Maria Gema Fernandez Miguel, Madrid (ES); Manuel Angel Gonzalez De La Pena, Madrid (ES); Rosa Ana Garcia Castro, Madrid (ES); Mariano Garcia Arranz, Madrid (ES); Damian Garcia-Olmo, Madrid (ES)

(73) Assignees: TIGENIX, S.A.U., Madrid (ES); UNIVERSIDAD AUTONOMA DE MADRID, Madrid (ES)

( * ) Notice: Subject to any disclaimer, the term of this patent is extended or adjusted under 35 U.S.C. 154(b) by 0 days.

(21) Appl. No.: 14/017,152

(22) Filed: Sep. 3, 2013

(65) Prior Publication Data
US 2014/0072539 A1 Mar. 13, 2014

Related U.S. Application Data

(63) Continuation of application No. 13/457,053, filed on Apr. 26, 2012, now abandoned, which is a continuation of application No. 11/167,061, filed on Jun. 24, 2005, now abandoned, which is a continuation-in-part of application No. 11/065,461, filed on Feb. 25, 2005, now abandoned, and a continuation-in-part of application No. 11/056,241, filed on Feb. 14, 2005, now abandoned.

(30) Foreign Application Priority Data

Aug. 25, 2004 (ES) .................................. 200402083
Oct. 4, 2004 (ES) .................................. 200402355

(51) Int. Cl.

| A61L 27/38 | (2006.01) |
|---|---|
| A61L 27/36 | (2006.01) |
| A61K 35/35 | (2015.01) |
| A61L 24/10 | (2006.01) |
| C12N 5/0775 | (2010.01) |
| A61B 17/16 | (2006.01) |
| A61K 45/06 | (2006.01) |
| A61L 24/00 | (2006.01) |
| A61B 17/32 | (2006.01) |
| A61K 35/12 | (2015.01) |

(52) U.S. Cl.
CPC .......... *A61K 35/35* (2013.01); *A61B 17/1659* (2013.01); *A61B 17/32* (2013.01); *A61K 45/06* (2013.01); *A61L 24/0015* (2013.01); *A61L 24/106* (2013.01); *A61L 27/3604* (2013.01); *A61L 27/3834* (2013.01); *A61L 27/3839* (2013.01); *A61L 27/3869* (2013.01); *A61L 27/3895* (2013.01); *C12N 5/0667* (2013.01); *A61B 2017/320008* (2013.01); *A61K 35/12* (2013.01); *A61L 2300/64* (2013.01); *C12N 2509/00* (2013.01); *C12N 2510/00* (2013.01); *C12N 2533/56* (2013.01)

(58) Field of Classification Search
None
See application file for complete search history.

(56) References Cited

U.S. PATENT DOCUMENTS

| 4,298,002 | A | 11/1981 | Ronel et al. |
|---|---|---|---|
| 5,145,770 | A † | 9/1992 | Tubo |
| 5,324,656 | A | 6/1994 | Ham et al. |
| 5,855,619 | A | 1/1999 | Caplan et al. |
| 5,976,526 | A | 11/1999 | Atala |
| 6,174,333 | B1 † | 1/2001 | Kadiyala |
| 6,541,028 | B1 * | 4/2003 | Kuri-Harcuch et al. ..... 424/443 |
| 6,555,374 | B1 | 4/2003 | Gimble et al. |
| 6,777,231 | B1 | 8/2004 | Katz et al. |
| 7,078,232 | B2 | 7/2006 | Konkle et al. |
| 7,470,537 | B2 | 12/2008 | Hendrik et al. |
| 7,645,229 | B2 | 1/2010 | Armstrong |
| 7,732,126 | B2 | 6/2010 | Zhang et al. |
| 8,440,177 | B2 | 5/2013 | de la Peña et al. |
| 8,679,834 | B2 | 3/2014 | Lombardo et al. |
| 8,790,680 | B2 | 7/2014 | Chancellor et al. |
| 9,074,190 | B2 | 7/2015 | Yoshimura |
| 9,200,255 | B2 | 12/2015 | Halvorsen |
| 9,631,176 | B2 | 4/2017 | Yoshimura et al. |
| 9,744,267 | B2 | 8/2017 | Chancellor et al. |
| 9,943,550 | B2 | 4/2018 | Buscher et al. |
| 2002/0044923 | A1 | 4/2002 | Mosca et al. |
| 2002/0085996 | A1 | 7/2002 | McIntosh et al. |
| 2003/0054331 | A1 | 3/2003 | Fraser et al. |

(Continued)

FOREIGN PATENT DOCUMENTS

| EP | 1634608 A1 | 3/2006 |
|---|---|---|
| EP | 1803472 A1 | 7/2007 |

(Continued)

OTHER PUBLICATIONS

Walmsley et al. Tissue Engineer Part A 2015;21:2281-91.*

(Continued)

*Primary Examiner* — Maria G Leavitt

(74) *Attorney, Agent, or Firm* — Morrison & Foerster LLP

(57) ABSTRACT

Provided herein are novel methods and compositions utilizing adipose tissue-derived stromal stem cells for treating fistulae.

14 Claims, 8 Drawing Sheets

(56) References Cited

U.S. PATENT DOCUMENTS

| | | |
|---|---|---|
| 2003/0082152 A1 | 5/2003 | Hedrick et al. |
| 2003/0152558 A1 | 8/2003 | Luft et al. |
| 2004/0180040 A1 | 9/2004 | Phillips et al. |
| 2005/0019911 A1 | 1/2005 | Gronthos et al. |
| 2005/0048644 A1 | 3/2005 | Hedrick et al. |
| 2005/0054098 A1 | 3/2005 | Mistry et al. |
| 2005/0153442 A1 | 7/2005 | Katz et al. |
| 2005/0221327 A1 | 10/2005 | Lundgren-Akerlund |
| 2005/0239897 A1 | 10/2005 | Pittenger et al. |
| 2005/0244963 A1 | 11/2005 | Teplyashin |
| 2005/0282275 A1 | 12/2005 | Katz et al. |
| 2006/0045872 A1 | 3/2006 | Miguel et al. |
| 2006/0047312 A1 | 3/2006 | Garcia Olmo et al. |
| 2006/0073124 A1 | 4/2006 | Garcia Castro et al. |
| 2006/0286089 A1 | 12/2006 | Berenson et al. |
| 2007/0178071 A1 | 8/2007 | Westenfelder et al. |
| 2007/0248580 A1 | 10/2007 | Garcia Castro et al. |
| 2008/0050349 A1 | 2/2008 | Steward |
| 2008/0095749 A1 | 4/2008 | Aggarwal et al. |
| 2009/0292311 A1 | 11/2009 | Garcia Olmo et al. |
| 2010/0098669 A1* | 4/2010 | Fernandez Miguel et al. ............. 424/93.7 |
| 2010/0209403 A1 | 8/2010 | Meiron et al. |
| 2011/0262402 A1 | 10/2011 | Kuroda et al. |
| 2012/0269774 A1 | 10/2012 | Ichim et al. |
| 2014/0134140 A1 | 5/2014 | Caplan et al. |
| 2017/0296585 A1 | 10/2017 | Garcia Castro et al. |

FOREIGN PATENT DOCUMENTS

| | | |
|---|---|---|
| EP | 2292737 A1 | 3/2011 |
| EP | 2292736 B1 | 1/2015 |
| EP | 1926813 B1 | 6/2016 |
| JP | 2002537849 A | 11/2002 |
| WO | WO-1996023058 A1 | 8/1996 |
| WO | WO-1999028444 A1 | 6/1999 |
| WO | WO-2000053795 A1 | 9/2000 |
| WO | 2002/067867 A2 | 9/2002 |
| WO | 2003/022988 A2 | 3/2003 |
| WO | 2003/024215 A1 † | 3/2003 |
| WO | WO-2003040346 A2 | 5/2003 |
| WO | WO-2004111208 A1 | 12/2004 |
| WO | 2005/035738 A1 | 4/2005 |
| WO | 2005/042730 A2 | 5/2005 |
| WO | 2005/062857 A2 | 7/2005 |
| WO | WO-2005093044 A1 | 10/2005 |
| WO | 2006/037649 A1 | 4/2006 |
| WO | 2006/136244 A2 | 12/2006 |
| WO | WO-2008036374 A2 | 3/2008 |
| WO | WO-2008116157 A2 | 9/2008 |
| WO | WO-2009050282 A1 | 4/2009 |
| WO | WO-2010/112662 A1 | 10/2010 |
| WO | WO-2012095743 A2 | 7/2012 |
| WO | WO-2012123401 A1 | 9/2012 |
| WO | WO 2014/140362 A2 | 9/2014 |
| WO | WO-2014207679 A1 | 12/2014 |

OTHER PUBLICATIONS

Kotobuki et al Cultured Autologous Human Cells for Hard Tissue Regeneration: Preparation and Characterization of Mesenchymal Stem Cells from Bone Marrow 2004; Artificial Organs 28(1):33-39.*

Cryopreserved | Definition of Cryopreserved by Merriam-Webster pp. 1-9; Downloaded on May 16, 2019.*

Cellzdirect, Inc., A Delaware 2015; pp. 1-17.*

Requirement for Restriction/Election received for U.S. Appl. No. 11/993,859, dated Jul. 5, 2012, 11 pages.

Non-Final Office Action received for U.S. Appl. No. 11/993,859, dated Apr. 22, 2013, 23 pages.

Final Office Action received for U.S. Appl. No. 11/993,059, dated Nov. 25, 2013, 29 pages.

Le Blanc et al., "Immunobiology of Human Mesenchymal Stem Cells and Future Use in Hematopoietic Stem Cell Transplatation", Biology of Blood and Marrow Transplantation, vol. 11, No. 5, May 2005, pp. 321-334.

De La Portilla et al., "Expanded Allogeneic Adipose-Derived Stem Cells (eASCs) for the Treatment of Complex Perianal Fistula in Crohn's Disease: Results from a Multicenter Phase I/IIa Clinical Trial", International Journal of Colorectal Disease, vol. 28, No. 3, Mar. 2013, pp. 313-323.

Garcia-Olmo et al., "A Phase I Clinical Trial of the Treatment of Crohn's Fistula by Adipose Mesenchymal Stem Cell Transplantation", Diseases of the Colon and Rectum, vol. 48, No. 7, Jul. 2005, pp. 1416-1423.

Guilak et al., "Clonal Analysis of the Differentiation Potential of Human Adipose-Derived Adult Stem Cells", Journal of Cellular Physiology, vol. 206, No. 1, Jan. 2006, pp. 229-237.

Herreros et al., "Autologous Expanded Adipose-Derived Stem Cells for the Treatment of Complex Cryptoglandular Perianal Fistulas: a Phase III Randomized Clinical Trial (FATT 1: Fistula Advanced Therapy Trial 1) and Long-Term Evaluation", Diseases of the Colon & Rectum, vol. 55, No. 7, Jul. 2012, pp. 762-772.

Lendeckel et al., "Autologous Stem Cells (Adipose) and Fibrin Glue Used to Treat Widespread Traumatic Calvarial Defects: Case Report", Journal of Cranio Maxillofacial Surgery, vol. 32, No. 6, Dec. 2004, pp. 370-373.

Wan Safwani et al., "The Changes of Stemness Biomarkers Expression in Human Adipose-Derived Stem Cells During Long-Terrn Manipulation", Biotechnology and Applied Biochemistry, vol. 58, No. 4, Jul./Aug. 2011, pp. 261-270.

Zhao et al., "The Effect of Serial Passaging on the Proliferation and Differentiation of Bovine Adipose-Derived Stem Cells", Cells Tissues Organs, vol. 195, 2012, pp. 414-427.

"American Gastroenterological Association Medical Position Statement: Perianal Crohn's Disease", Gastroenterology, vol. 125, No. 5, Nov. 2003, pp. 1503-1507.

Non-Final Office Action received for U.S. Appl. No. 11/167,061, dated Feb. 3, 2011, 9 pages.

Final Office Acton received for U.S. Appl. No. 11/167,061, dated Oct. 26, 2011, 8 pages.

Abkowitz, Janis L., "Can Human Hematopoietic Stem Cells Become Skin, Gut, or Liver Cells?", The New England Journal of Medicine, vol. 346, No. 10, Mar. 7, 2002, pp. 770-772.

Beresford et al., "Evidence for an Inverse Relationship Between the Differentiation of Adipocytic and Osteogenic Cells in Rat Marrow Stromel Cell Cultures", Journal of Cell Science, vol. 102, 1992, pp. 341-351.

Caplan et al., "Mesenchymal Stem Cells Building Blocks to Molecular Medicine in the 21st Century", Trends in Molecular Medicine, vol. 7, No. 6, Jun. 2001, pp. 259-264.

Caplan, Arnold I., "Mesenchymal Stem Cells", Journal of Orthopedic Research, vol. 9, No. 5. 1991, pp. 641-650.

Cowan et al., "Adipose-Derived Adult Stromal Cells Heal Critical-Size Mouse Calvarial Defects", Nature Biotechnology, vol. 22, No. 5, May 2004, pp. 560-567.

De Ugarte et al., "Comparison of Multi-Lineage Cells from Human Adipose Tissue and Bone Marrow", Cells Tissues Organs, vol. 174, 2003, pp. 101-109.

Friedenstein et al., "Fibroblast Precursors in Normal and Irradiated Mouse Hematopoietic Organs", Exp. Hemat., vol. 4, 1976, pp. 267-274.

Garcia-Olmo et al., "Autologous Stem Cell Transplantation for Treatment of Rectovaginal Fistula in Perianal Crohn's Disease: A New Cell-Based Therapy", Int. J. Colorectoral Dis., vol. 18, 2003, pp. 451-454.

Garcia-Olmo et al., "The Vulture and Stem Cells", The New England Journal of Medicine, vol. 349, No. 15, Oct. 9, 2003, pp. 1480-1481.

Haynesworth et al., "Characterization of Cells with Osteogenic Potential from Human Marrow", Bone, vol. 13, 1992, pp. 81-88.

Ivanova et al., "A Stem Cell Molecular Signature", Science, vol. 298, Oct. 18, 2002, pp. 601-604.

(56) References Cited

OTHER PUBLICATIONS

Jiang et al., "Multipotent Progenitor Cells can be Isolated from Postnatal Murine Bone Marrow, Muscle, and Brain", Experimental Hematology, vol. 30, 2002, pp. 896-904.
Levy et al., "Managment of Internal Fistulas in Crohn's Disease", Inflammatory Bowel Diseases, vol. 8, No. 2, Mar. 2002, pp. 106-111.
Matsubara, Hiroaki, "Risk to the Coronary Arteries of Intracoronary Stem Cell Infusion and G-CSF Cytokine Therapy", The Lancet, vol. 363, Mar. 6, 2004, pp. 746-747.
Mizuno et al., "Myogenic Differentiation by Human Processed Lipoaspirate Cells", Plastic and Reconstructive Sugery, vol. 109, No. 1, Jan. 2002, pp. 199-209.
Morrisson et al., "The Biology of Hematopoietic Stem Cells", Annu. Rev. Cell Dev. Biol., vol. 11, 1995, pp. 35-71.
Osawa et al., "Long-Term Lymphohematopoietic Reconstitution by a Single CD34-Low/Negative Hematopoietic Stem Cell", Science, vol. 273, Jul. 12, 1996, pp. 242-245.
Penninckx et al., "Advancedment Flap Plasty for the Closure of Anal and Recto-Vaginal Fistulas in Crohn's Disease", Acta Gastro-Enterolgica Belgica, vol. 64, Apr.-Jun. 2001, pp. 223-226.
Phillips, R. L., "Investigating the Genetic Control of Stem Cell Behavior", Curr. Top. Microbiol. Immunol., vol. 251, 2000, pp. 13-19.
Pitienger et al., "Multilineage Potential of Adult Human Mesenchymal Stem Cells", Science, vol. 284, Apr. 2, 1999, pp. 143-147.
Ramalho-Santos et al., "Stemness: Transcriptional Profiling of Embryonic and Adult Stem Cells", Science, vol. 298, Oct. 18, 2002, pp. 597-600.
Rogers et al., "Differentiation Factors Induce Expression of Muscle, Fat, Cartilage, and Bone in a Clone of Mouse Pluripotent Mesenchymal Stem Cells", The American Surgeon, vol. 61, No. 3, Mar. 1995, pp. 231-236.
Rius et al., "Gacilis Transposition in Complicated Perianal Fistula and Unhealed Perineal Wounds in Crohn's Disease", Eur. J. Surg., vol. 166, 2000, pp. 218-222.
Sanchez-Ramos et al., "Adult Bone Marrow Stromal Cells Differentiate into Neural Cells in Vitro", Experimental Neurology, vol. 164, 2000, pp. 247-256.
Stanford el al., "Rapidly Forming Apatitic Mineral in an Osteoblastic Cell Line (UMR 106-01 BSP)", The Journal of Biological Chemistry, vol. 270, No. 16, Apr. 21, 1995, pp. 9420-9428.
Wakitani et al., "Myogenic Cells Derived from Rat Bone Marrow Mesenchymal Stem Cells Exposed to 5-Azacytidine", Muscle & Nerve, vol. 18, Dec. 1995, pp. 1417-1426.
Yoo et al., "The Role of Osteochondral Progenitor Cells in Fracture Repair", Clinical Orthopaedics and Related Research, vol. 355S, Oct. 1998, pp. S73-S81.
Zuk et al., "Multilineage Cells from Human Adipose Tissue: Implications for Cell-Based Therapies", Tissue Engineering, vol. 7, No. 2, 2001, pp. 211-228.
Zannettino et al., "Multipotential Human Adipos-Derived Stromal Stem Cells Exhibit a Perivascular Phenotype In Vitro and In Vivo", J. Cell. Phys., vol. 214, 2008, pp. 413-421.
Zhao et al., "The Effect of Serial Passaging on the Proliferation and Differentiation of Bovine Adipose-Derived Stem Cells", Cells Tissues Organs., vol. 195, No. 5, 2011, pp. 414-427.
Zilberfarb et al., "Human Immortalized Brown Adipocytes Express Functional Beta3-Adrenoceptor Coupled to Lipolysis", J. Cell. Sci., vol. 110, 1997, pp. 801-807.
Zimmerlin et al., "Stromal Vascular Progenitors in Adult Human Adipose Tissue", Cytometry, vol. 77A, No. 1, 2010, pp. 22-30.
Zuk et al., "Human Adipose Tissue is a Source of Multipotent Stem Cells", Molecular Biology of the Cell, vol. 13, 2002, pp. 4279-4295.
Zun-Li et al., "A Schwann Cell-Seeded Intrinsic Framework and its Satisfactory Biocompatibility for a Bioartificial Nerve Graft", Microsurgery, vol. 21, No. 1, 2001, pp. 6-11.
Declaration by Dr. Mario Delgado dated Mar. 26, 2011, submitted in 95/001, 592, 27 pages.

Declaration by Dr. Mario Delgado dated Sep. 30, 2011, submitted in 95/001, 592, 27 pages.
Declaration of Farshid Guilak Pursuant to 37 CFR § 1.132, filed Aug. 31, 2011, 19 pages.
"COL2A1 Collagen, Type II, Alpha 1 (*Homo sapiens*)", Available online at: <http://www.ncbi.nlm.nih.gov/gene/1280>, Feb. 24, 2011, 8 pages.
"Durham Firm Sells Technology, Shuts Down; Md Fund's Startup to Develop Artecel's Stem Cell Science", LexisNexis, The Herald-Sun (Durham, NC), Apr. 11, 2003, 2 pages.
"Isolation, Propagation and Characterization of Human Mesenchymal Stem Cells", Final Report N-01191, Vivotecnia Research S.L., Mar. 23, 2011, 47 pages.
Committee for Advanced Therapies, "Reflection Paper on Stem Cell-Based Medicinal Products", European Medicines Agency, EMA/CAT/571134/2009, Jan. 14, 2011, 14 pages.
Entenmann et al., "Relationship between Replication and Differentiation in Cultured Human Adipocyte Precursor Cells", Am. J. Physiol., vol. 270 (4 Pt 1), 1996, pp. C1011-C1016.
Notice of Allowance received for U.S. Appl. No. 11/993,859, dated Aug. 12, 2014, 9 pages.
Notice of Allowance received for U.S. Appl. No. 11/993,859, dated May 21, 2014, 10 pages.
Third Party Submissions dated May 15, 2014, submitted in U.S. Appl. No. 14/017,152, 13 pages.
Astori, et al., "In Vitro' and Multicolor Phenotypic Characterization of Cell Subpopulations Identified in Fresh Human Adipose Tissue Stromal Vascular Fraction and in the Derived Mesenchymal Stem Cells", Journal of Translational Medicine, vol. 5, 2007, pp. 1-10.
Awad et al., "Chondrogenic Differentiation of Adipose-Derived Adult Stem Cells Agarose, Alginate, and Gelatin Scaffolds", Biomaterials, vol. 25, No. 16, 2004, pp. 3211-3222.
Barry, et al., "Mesenchymal Stem Cells: Clinical Applications and Biological Characterization", Int. J. Biochem. Cell Biol. vol. 36, No. 4, 2004, pp. 568-584.
Cai et al., "Adipose Stem Cells Originate from Perivascular Cells", Biol. Cell, vol. 103, No. 9, 2011, pp. 435-447.
Cao et al., "Human Adipose Tissue-Derived Stem Cells Differentiate Into Endothelial Cells in Vitro and Improve Postnatal Neovascularization in Vivo", Biochem. and Biophys. Res. Comm., vol. 332, No. 2, 2005, pp. 370-379.
Caplan A. I., "Mesenchymal Stem Cells: Cell-Based Reconstructive Therapy in Orthopedics", Tiss. Eng., vol. 11, No. (7-8), 2005. pp. 1198-1211.
Chandra et al., "Generation of Pancreatic Hormone-Expressing Islet-Like Cell Aggregates from Murine Adipose Tissue-Derived Stem Cells", Stem Cells, vol. 27, 2009, pp. 1941-1953.
Crisan et al., "A Perivascular Origin for Mesenchymal Stem Cells in Multiple Human Organs", Cell Stem Cell, vol. 3, No. 3, 2008, pp. 301-313.
Estes et al., "Monolayer Cell Expansion Conditions Affect the Chondrogenic Potential of Adipose-Derived Stem Cells", Biotechnology and Bioengineering, vol. 99, No. 4, Mar. 1, 2008, pp. 986-995.
Gimble J. M., "Adipose Tissue-Derived Therapeutics", Exp. Op. Biol. Ther., vol. 3, No. 5, 2003, pp, 705-713.
Gimble et al., "Differentiation Potential of Adipose Derived Adult Stem (ADAS) Cells", Curr. Top Dev. Biol., vol. 58, 2003, pp. 137-160.
Gimble et al., "Isolation and Growth of Stem Cells", Chapter 6 in Tissue Engineering, 2011, pp. 93-111.
Gomillion, et al., "Stem Cells and Adipose Tissue Engineering", Biomaterials, vol. 27, 2006, pp. 6052-6063.
Halme et al., "FDA Regulation of Stem-Cell-Based Therapies", NEJM, vol. 355, No. 16, 2006, pp. 1730-1735.
Hauner et al., "Promoting Effect of Glucocorticoids on the Differentiation of Human Adipocyte Precursor Cells Cultured in a Chemically Defined Medium", J. Clin Invest., vol. 84, 1989, pp. 1663-1670.
Ikegame et al., "Comparison of Mesenchymal Stem Cells from Adipose Tissue and Bone Marrow for Ischemic Stroke Therapy", Cytotherapy, vol. 13, No. 6, 2011, pp. 675-685.

(56) References Cited

OTHER PUBLICATIONS

Ishimura et al., "Differentiation of Adipose-derived Stromal Vascular Fraction Culture Cells into Chondrocytes Using the Method of Cell Sorting with a Mesenchymal Stem Cell Marker", Tohoku J. Exp. Med., vol. 216, 2008, pp. 149-156.
Kern et al., "Comparative Analysis of Mesenchymal Stem Cells from Bone Marrow, Umbilical Cord Blood, or Adipose Tissue", Stem Cells, vol. 24, 2006, pp. 1294-1301.
Kim et al., "Direct Comparison of Human Mesenchymal Stem Cells Derived From Adipose Tissues and Bone Marrow in Mediating Neovascularization in Response to Vascular Ischemia", Cell Physiol. Biochem., vol. 20, 2007, pp. 867-876.
Kurtia et al., "Influences of Centrifugation on Cells and Tissues in Liposuction Aspirates: Optimized Centrifugation for Lipotransfer and Cell Isolation", Plast. Reconstr. Surg., vol. 121, No. 3, 2008, pp. 1033-1041.
Lee et al., "Characterization and Expression Analysis of Mesenchymal Stem Cells from Human Bone Marrow and Adipose Tissue", Cell. Phys. Biochem., vol. 14, 2004, pp. 311-324.
Lund et al., "Effect of Growth Media and Serum Replacements on the Proliferation and Differentiation of Adipose-Derived Stem Cells", Cytotherapy, vol. 11, No. 2, 2009, pp. 189-197.
McIntosh et al., "The Immunogenicity of Human Adipose-Derived Cells: Temporal Changes in Vitro", Stem Cells, vol. 24, 2006, pp. 1246-1253.
Minteer et al., "Adipose-Derived Mesenchymal Stem Cells: Biology and Potential Applications", Adv. Biochem. Eng. Biotechnol., vol. 129, 2013, pp. 59-71.
Pascual et al., "Adipose-Derived Mesenchymal Stem Cells in Biosutures do not Improve Healing of Experimental Colonic Anastomoses", Brit. J. Surg., vol. 95, No. 9, 2008, pp. 1180-1184.
Rajshekhar et al., "IFATS Collection: Adipose Stromal Cell Differentiation is Reduced by Endothelial Cell Contact and Paracrine Communication: Role of Canonical Wnt Signaling", Stem Cells., vol. 26, No. 10, 2008, pp. 2674-2681.
Rojewski et al., "Phenotypic Characterization of Mesenchymal Stem Cells from Various Tissues", Trans. Med. Hemother., vol. 35, 2007, pp. 168-184.
Roughley et al., "The Structure and Function of Cartilage Proteoglycans", Europ. Cells and Materials, vol. 12, 2006, pp. 92-101.
Schreml et al., "Harvesting Human Adipose Tissue-Derived Adult Stem Cells: Resection Versus Liposuction", Cytotherapy, vol. 11, No. 7, 2009, pp. 947-957.
Thankamony et al., "Enforced Hematopoietic Cell E- and L-Selectin Ligand (HCELL) Expression Primes Transendothelial Migration of Human Mesenchymal Stem Cells", PNAS, vol. 108, 2011, pp. 2258-2263.
Tholpady et al., "Adipose Tissue: Stem Cells and Beyond", Clin. Plast. Surg., vol. 33, No. 1, 2006, pp. 55-62.
Torensma et al., "The Impact of Cell Source, Culture Methodology, Culture Location and Individual Donors on Gene Expression Profiles of Bone Marrow-Derived and Adipose-Derived Stromal Cells", Stem Cell Dev., vol. 22, No. 7, 2013, pp. 1086-1096.
Van et al., "Cytological and Enzymological Characterization of Adult Human Adipocyte Precursors in Culture", J. Clin. Invest., vol. 58, No. 3, 1976, pp. 699-704.
Wabitsch et al., "IGF-I- and IGFBP-3-Expression in Cultured Human Preadipocytes and Adipocytes", Horm. Metab. Res., vol. 32, 2000, pp. 555-559.
Wagner et al., "Comparative Characteristics of Mesenchymal Stem Cells from Human Bone Marrow, Adipose Tissue, and Umbilical Cord Blood", Experimental Hematology, vol. 33, 2005, pp. 1402-1416.
Winter et al., "Cartilage-Like Gene Expression in Differentiated Human Stem Cell Spheroids. A Comparison of Bone Marrow-Derived and Adipose Tissue-Derived Stromal Cells", Arthritis and Rheumatism vol. 48, No. 2, 2003, pp. 418-429.

Xu et al., "Connective Tissue Growth Factor in Regulation of RhoA Mediated Cytoskeletal Tension Associated Osteogenesis of Mouse Adipose-Derived Stromal Cells", PLos One., vol. 5, No. 6, 2010, e11279 page.
Yoshimura et al., "Characterization of Freshly Isolated and Cultured Cells Derived From the Fatty and Fluid Portions of Liposuction Aspirates", Journal of Cellular Physiology, vol. 208, 2006, pp. 64-76.
Young et al., "Use of Mesenchymal Stem Cells in a Collagen Matrix for Achilles Tendon Repair", J. Ortho. Res., vol. 16, No. 4, 1998, pp. 406-413.
Non-Final Office Action received for U.S. Appl. No. 14/538,681, dated Aug. 17, 2016, 30 pages.
Anonymous (2013). "TiGenix Press Release 2013," Available at URL: http://www.tigenix.comjenjpages/11/2013, 2 pages.
Anonymous (2015). "Cx601 (Alofisel) for complex perianal fistula in adults with non-active or mildly-active luminal Chron's disease—second line," National Institute for Health Research Horizon Scanning Centre, 8 pages.
Anonymous (2015). "TiGenix announces Cx601 meets primary endpoint in pivotal Phase III trial," TiGenix press release, 5 pages.
Anonymous (2016). "TiGenix announces positive 52-week Phase III results of Cx601 in complex perianal fistulas in Crohn's disease patients," TiGenix press release, 3 pages.
Anonymous, "Cx611 in RA", available online at <http://www.tigenix.com/en/download/?s=rNXU8Ivo7ZUjEybwArESBX4S%2BkEKDIBvQYuoUTu%2FQzzXtBQzMAI7TEC318DkwthFj%2BYyaSGvZW9cSU6K1 0OQDQ%3D%3D>, 2013, by TiGenix, 47 pages.
Anonymous, "TiGenix Completes EUR 6.5 million Capital Increase", available online at <http://www.tigenix.com/en/download/?s=Z26Ua20y8Za%2FoG0QmRK8XeAKmi8idp%2FrsRyPi2HQV9vBBMGzfBT6aFG%2FibaP7g55QAMhyS0qtkaBEjVvEBPcAg%3D%3D>, Jul. 26, 2013, by TiGenix, pp. 1-2.
Anonymous, "TiGenix Reports Positive Phase IIa Study Results in Refractory Rheumatoid Arthritis with Allogeneic Stem Cell Product Cx611", retrieved from <http://www.tigenix.com/public/uploads/pdf/en/f5177d809eca202.40307502_TiGenix%20Cx611%20Phase%20IIa%20results%20Final.pdf>, Apr. 22, 2013, by TiGenix, 3 pages.
Bochev et al., "Mesenchymal stem cells from human bone marrow or adipose tissue differently modulate mitogen-stimulated B-cell immunoglobulin production in vitro", Cell Biology International, 2008, vol. 32, 384-393.
Bourin et al., "Stromal Cells from the Adipose Tissue-derived Stromal Vascular Fraction and Culture Expanded Adipose Tissue-derived Stromal/stem Cells: A Joint Statement of The International Federation for Adipose Therapeutics and Science (IFATS) and The International Society for Cellular Therapy (ISCT)", Cytotherapy, vol. 15, No. 6, Jun. 1, 2013, pp. 641-648.
Byk, Tamara, et al., "Lipofectamine and Related Cationic Lipids Strongly Improve Adenoviral Infection Efficiency of Primitive Human Hematopoietic Cells," Human Gene Therapy, 1998, pp. 2493-2502, vol. 9.
Cho et al. (2015). "Long-term results of adipose-derived stem cell therapy for the treatment of Crohn's fistula," Stem Cells Transl Med., 4(5):532-7.
DelaRosa et al. (2009). "Requirement of IFN-gamma-mediated indoleamine 2,3-dioxygenase expression in the modulation of lymphocyte proliferation by human adipose-derived stem cells," Tissue Eng Part A. 15(10):2795-806.
Delarosa, "Mesenchymal Stem Cells as Therapeutic Agents of Inflammatory and Autoimmune Diseases", Current Opinion in Biotechnology, vol. 23, Jun. 2012, No. 6, pp. 978-983.
Garcia-Olmo et al. (2015). "Cumulative Evidence That Mesenchymal Stem Cells Promote Healing of Perianal Fistulas of Patients With Crohn's Disease—Going From Bench to Bedside," American Gastroenterological Association Institute, vol. 149, Issue 4, pp. 853-857.
Gonzalez-Rey et al., "Human Adipose-derived Mesenchymal Stem Cells reduce Inflammatory and T Cell Responses and Induce Regulatory T Cells in Vitro in Rheumatoid Arthritis", Annals of the Rheumatic Diseases, vol. 69, Jan. 2010, No. 1, pp. 241-248.

(56) References Cited

OTHER PUBLICATIONS

Guadalajara et al. (2016). "Prospect of Cell Therapy for Treating Perianal Fistula, Including Crohn's Disease," Int J Stem Cell Res Ther, vol. 3, Issue 1, pp. 028, 7pages.
Ichim et al., "Autologous Stromal Vascular Fraction Cells: A Tool for Facilitating Tolerance in Rheumatic Disease", Cellular Immunology, vol. 264, No. 1, Apr. 2010, pp. 7-17.
Ivanova-Todorova, E. "Adipose tissue-derived mesenchymal stem cells are more potent suppressors of dendritic cells differentiation compared to bone marrow-derived mesenchymal stem cells." Immunology Letters, 2009, vol. 126, pp. 37-42.
Kan, I., et al., Integral Therapeutic Potential of Bone Marrow Mesenchymal Stem Cells, Current Drug Targets, 2005, pp. 31-41, vol. 6.
Kim et al., "Paradoxical Effects of Human Adipose Tissue-Derived Mesenchymal Stem Cells on Progression of Experimental Arthritis in SKG Mice", Cellular Immunology, vol. 292, Nov. 2014, pp. 94-101.
Kim, Jeong-Min, et al., "Systemic transplantation of human adipose stem cells attenuated cerebral inflammation and degeneration in a hemorrhagic stroke model," Brain Research, 2007, pp. 43-50, vol. 1183.
Krasnodembskaya et al., "Antibacterial Effect of Human Mesenchymal Stem Cells is Mediated in Part from Secretion of the Antimicrobial Peptide LL-37", Stem Cells, vol. 28, No. 12, Dec. 2010, pp. 2229-2238.
Le Blanc, K. et al., "Immunomodulation by mesenchymal stem cells and clinical experience," Journal of Internal Medicine, 2007, pp. 509-525, vol. 262.
Lee et al., "Preclinical Efficacy and Mechanisms of Mesenchymal Stem Cells in Animal Models of Autoimmune Diseases", Immune Network, vol. 14, No. 2, Apr. 2014, pp. 81-88.
Li et al., "Human Umbilical Cord Mesenchymal Stem Cells Reduce Systemic Inflammation and Attenuate LPS-Induced Acute Lung Injury in Rats", Journal of Inflammation, vol. 9, No. 33, Sep. 2012, pp. 1-11.
Lopez-Santalla et al. (2015). "Human Adipose-Derived Mesenchymal Stem Cells Modulate Experimental Autoimmune Arthritis by Modifying Early Adaptive T Cell Responses," Stem Cells, 33: 3493-3503.
Mei et al. (2007). "Prevention of LPS-Induced Acute Lung Injury in Mice by Mesenchymal Stem cells Overexpressing Angiopoietin 1," PLoS Medicine, vol. 4, Issue 9, pp. 1525-1537.
Mei et al., "Mesenchymal Stem Cells Reduce Inflammation while Enhancing Bacterial Clearance and Improving Survival in Sepsis", American Journal of Respiratory and Critical Care Medicine, vol. 182, Oct. 2010, pp. 1047-1057.
Molendijk et al. (2015). "Allogeneic Bone Marrow—Derived Mesenchymal Stromal Cells Promote Healing of Refractory Perianal Fistulas in Patients With Crohn's Disease," Gastroenterology, vol. 149, pp. 918-927.
Nemeth et al., "Bone Marrow Stromal Cells Attenuate Sepsis via Prostaglandin E2-Dependent Reprogramming of Host Macrophages to increase their Interleukin-10 Production", Nature Medicine, vol. 15, No. 1, Jan. 2009, pp. 42-49.
Panes et al. (2016). "A phase III randomised controlled trial of Cx601, expanded allogeneic adipose-derived mesenchymal stem cells (eASC), for complex perianal fistulas in Crohn's disease," Journal of Crohn's and Colitis, Oral presentations, pp. S1.
Panes et al. (2016). "Expanded allogeneic adipose-derived mesenchymal stem cells (Cx601) for complex perianal fistulas in Crohn's disease: a phase 3 randomised, double-blind controlled trial," Lancet. 388(10051):1281-90.
Panes et al. (2017). "Cx601, Allogeneic Expanded Adipose-derived Mesenchymal Stem Cells (EASC), for Complex Perianal Fistulas in Crohn's Disease: Long-term Results from a Phase III Randomized Controlled Trial," AGA Abstracts, pp. S-187.
Park et al. (2012). "Adipose-Derived Stem Cell Treatment for Persistent Perineal Wound in Complex Crohn's Perianal Abscess/Fistula," Gastroenterology, vol. 142, Issue 5, Supplement 1, pp. S-76, AGA Abstract 329.
Park et al. (2014). "Allogeneic Adipose-Derived Stem Cells for the Treatment of Crohn's Perianal Fistula: a Phase I/IIa Clinical Study," Gastroenterology, vol. 146, Issue 5, S-1016, SSAT Abstract 507.
Park et al. (2015). "Allogeneic adipose-derived stem cells for the treatment of perianal fistula in Crohn's disease: a pilot clinical trial," Colorectal Dis. 18(5):468-76.
Puissant et al., "Immunomodulatory effect of human adipose tissue-derived adult stem cells: comparison with bone marrow mesenchymal stem cells," British Journal of Haematology, 2005, pp. 118-129, vol. 129.
Roach et al., "Methods for the Isolation and Maintenance of Murine Embryonic Stem Cells," Methods in Molecular Biology, 2002, pp. 1-16, vol. 185.
Rodriguez et al., "Autologous Stromal Vascular Fraction Therapy for Rheumatoid Arthritis: Rationale and Clinical Safety", International Archives of Medicine, Biomed Central Ltd, vol. 5, No. 5, Feb. 8, 2012, pp. 1-9.
Sanz-Baro et al. (2015). "First-in-Human Case Study: Pregnancy in Women With Crohn's Perianal Fistula Treated With Adipose-Derived Stem Cells: A Safety Study," Stem Cells Transl Med., 4(6):598-602.
Schaffler et al., "Concise Review: Adipose Tissue-derived Stromal Cells—Basic and Clinical Implications for Novel Cell-based Therapies", Stem Cells, vol. 25, No. 4, Apr. 1, 2007, pp. 818-827.
Singer et al. (2011). "Mesenchymal stem cells: mechanisms of inflammation," Annu Rev Pathol. 6:457-78.
Tigenix (2016). "Cx601 Crohn's disease and perianal fistulas," Retrieved from http://tigenix.com/en/page/14/cx601, 5 pages.
Xu, Jianguo, et al., "Prevention of endotoxin-induced systemic response by bone marrow-derived mesenchymal stem cells in mice," American Journal of Physiology, Lung Cellular and Molecular Physiology, 2007, pp. L131-L141, vol. 293.
Yañez, Rosa, et al.; "Adipose Tissue-Derived Mesenchymal Stem Cells Have In Vivo Immunosuppressive Properties Applicable for the Control of the Graft-Versus-Host Disease," Stem Cells, 2006, pp. 2582-2591, vol. 24.
Aust, L. (2004). "Yield of human adipose-derived adult stem cells from liposuction aspirates," Cytotherapy, 6:7-14.
Author unknown, published by Datapharm, "Alofisel 5 million cells/mL suspension for injection—Summary of Product Characteristics". Downloaded May 23, 2019.
Barry et al. (2005). "Immunogenicity of Adult Mesenchymal Stem Cells: Lessons from the Fetal Allograft," Stem Cells Development, 14:252-265.
Barry et al. (2005). "Mesenchymal Stem Cell Transplantation for Tissue Repair," Seminars in Plastic Surgery, vol. 19, pp. 229-239.
Be the Match, Haploidentical Transplant, retrieved from the internet, Feb. 14, 2019: https://bethematch.org/patients-and-families/about-transplant/what-is-a-bone-marrow-transplant/haploidentical-transplant/.
Borowski et al., (2015). "Adipose Tissue-Derived Regenerative Cell-Enhanced Lipofilling for Treatment of Cryptoglandular Fistulae-in-Ano: The ALFA Technique," Surg Innov., 22(6):593-600.
Chung et al. (2004). "Cotransplantation of Marrow Stromal Cells May Prevent Lethal Graft-versus-Host Disease in Major Histocompatibility Complex Mismatched Murine Hematopoietic Stem Cell Transplantation," Int J Hematol., 80:370-376.
Coombs, A., (2008). "Questioning the self cell," Nature Reports Stem Cells, pp. 1-6, https://doi.org/10.1038/stemcells.2008.86.
Cui et al., (2005). "Human adipose derived stem cells suppress lymphocyte proliferation induced by cellular or nonspecific mitogenic stimuli," Zhonghua Yi Xue Za Zhi, 20;85(27):1890-4. English Abstract only p. 1.
Dave, Maneesh, et al. (2015). "Mesenchymal Stem Cell Therapy for Inflammatory Bowel Disease: A Systematic Review and Meta-analysis," Inflamm Bowel Dis., 21:2696-2702; doi:10.1097/MIB.0000000000000543.
Deans et al., (2000). "Mesenchymal stem cells: Biology and potential clinical uses," Experimental Hematology, 28:875-884.

(56) References Cited

OTHER PUBLICATIONS

Delarosa et al., (2012). "Human Adipose-Derived Stem Cells Impair Natural Killer Cell Function and Exhibit Low Susceptibility to Natural Killer-Mediated Lysis," Stem Cells and Development, 21:1333-1343.
Djouad et al. (2005). "Transcriptional profiles discriminate bone marrow-derived and synovium-derived Mesenchymal stem cells," Arthritis Research & Therapy, 7:1304-1315.
Djouad et al. (2005). "Reversal of the Immunosuppressive Properties of Mesenchymal Stem Cells by Tumor Necrosis Factor Alpha in Collagen-Induced Arthritis," Arthritis & Rheumatism 52(5):1595-1603.
Dominici et al., (2006). "Minimal criteria for defining multipotent mesenchymal stromal cells, The International Society for Cellular Therapy position statement." Cytotherapy, 8(4):315-317.
Duijvestein et al., (2010). "Autologous bone marrow-derived mesenchymal stromal cell treatment for refractory luminal Crohn's disease: results of a phase I study," Gut, 59:1662-1669.
Duran et al. (2016). "Stem cell-based therapies in inflammatory bowel disease: promises and pitfalls," Therapeutic Advances in Gastroenterology, 9:533-547.
El Atat, et al. (2016). "An Evaluation of the Sternness, Paracrine, and Tumorigenic Characteristics of Highly Expanded, Minimally Passaged Adipose-Derived Stem Cells," PLoS ONE 11(9): e0162332. p. 1-22.
EMA press release (2017). "New medicine to treat perianal fistulas in patients with Crohn's disease," 2 pages.
Galipeau, (2013). "The mesenchymal stromal cells dilemma—does a negative phase III trial of random donor mesenchymal stromal cells in steroid-resistant graft-versus-host disease represent a death knell or a bump in the road?," Cytotherapy, 15(1):2-8.
Garcia-Olmo et al. (2015). "Stem Cells in Perianal Crohn Disease: cumulative Evidence and How to Go From the Bench to the Bedside," Gastroenterology, 149(4):853-7.
Garcia-Olmo et al., (2009). "Treatment of enterocutaneous fistula in Crohn's Disease with adipose-derived stem cells: a comparison of protocols with and without cell expansion," Int J Colorectal Dis, 24:27-30.
Garcia-Olmo (2007). "Expanded adipose-derived stem cells (Cx401) for the treatment of complex perianal fistula, a phase II clinical trial," Gastroenterology, 2 pages.
Gonzalez et al., (2009). "Adipose-Derived Mesenchymal Stem Cells Alleviate Experimental Colitis by Inhibiting Inflammatory and Autoimmune Responses," Gastroenterology, 136:978-989.
Gonzalez et al., (2009). "Treatment of Experimental Arthritis by Inducing Immune Tolerance With Human Adipose-Derived Mesenchymal Stem Cells", Arthritis & Rheumatism, 60(4):1006-1019.
Gotherstrom et al., (2004). "Immunologic properties of human fetal mesenchymal stem cells," AM. J. Obs. Gyn., 190:239-45.
Gowda et al. (2013). "Production of Good Manufacturing Practice Grade Equine Adipose-derived Mesenchymal Stem Cells for Therapeutic Use," J. Stem Cell Res. Ther., 3(5):1-11.
Hall et al. (2013). "Mesenchymal stromal cells improve survival during sepsis in the absence of heme oxygenase-1: the importance of neutrophils," Stem Cells, 31(2):397-407.
Hattori et al., (2004). "Osteogenic Potential of Human Adipose Tissue-Derived Stromal Cells as an Alternative Stem Cell Source," Cells Tissues Organs, 178(1):2-12.
Hawkey et al. (2000). "Stem cell transplantation for inflammatory bowel disease: practical and ethical issues," Gut, 46:869-872.
Horwitz et al. (2002). "Isolated allogeneic bone marrow-derived mesenchymal cells engraft and stimulate growth in children with osteogenesis imperfecta: Implications for cell therapy of bone," PNAS, 99:8932-8937.
Horwitz et al. (2006). "Mesenchymal Stromal Cells," Curr Opin Hematol. 13(6): 419-425.
Jewett A. et al. (2010). "Strategies to Rescue Mesenchymal Stem Cells (MSCs) and Dental Pulp Stem Cells (DPSCs) from NK Cell Mediated Cytotoxicity," Plos One, 5(3): e9874, pp. 1-14.
Jorgensen et al. (2001). "Stem cells for repair of cartilage and bone: the next challenge in osteoarthritis and rheumatoid arthritis," Annals of the Rheumatic Diseases, 60:305-309.
Jorgensen et al. (2003). "Mesenchymal stem cells and rheumatoid arthritis," Joint Bone Spine, 70:483-485.
Jung, Dong-In et al. (2009). "A comparison of autologous and allogenic bone marrow-derived mesenchymal stem cell transplantation in canine spinal cord injury," Journal of the Neurological Sciences, 285:67-77.
Keating, A., (2006). "Mesenchymal stromal cells," Curr Opin Hematol, 13:419-425.
Kebriaei et al., (2009). "Adult Human Mesenchymal Stem Cells Added to Corticosteroid Therapy for the Treatment of Acute Graft-versus-Host Disease," Biol Blood Marrow Transplant, 15:804-811.
Kim, et al., (2007). "Role of CD9 in proliferation and proangiogenic action of human adipose-derived mesenchymal stem cells," Pflugers Arch., 455(2):283-96. Abstract Only.
Koc et al. (2001). "Mesenchymal stem cells: heading into the clinic," Bone Marrow Transplantation, 27:235-239.
Krampera et al., (2006). "Role for Interferon-gamma in the Immunomodulatory Activity of Human Bone Marrow Mesenchymal Stem Cells," Stem Cells, Translation and Clinical Research, 24:386-398.
Lazarus H. et al. (2000). "Role of Mesenchymal Stem Cells (MSC) in Allogeneic Transplantation: Early Phase I Clinical Results," Blood. The American Society of Hematology. US., 96(11) Part 01., p. 392A. Abstract only.
Lee et al. (2013). "Therapeutic Effects of Human Mesenchymal Stem Cells in Ex Vivo Human Lungs Injured with Live Bacteria," American Journal of Respiratory and Critical Care Medicine, 187(7):751-760.
Liao, Lian-Ming, et al., (2005). Application of Mesenchymal Stem Cell in Immunotherapy, Journal of Experimental Hematology, 13:158-163, English Abstract.
Maccario et al., (2005). "Interaction of human mesenchymal stem cells with cells involved in alloantigen-specific immune response favors the differentiation of CD4 T-cell subsets expressing a regulatory/suppressive phenotype," the Haematologica Journal, 90:516-525.
Maneesh (2014). "Nonmyeloablative Stem Cell Therapy for Perianal Fistulizing Crohn's Disease: A Systematic Review of Safety and Efficacy," Gastroenterology, 2 pages.
Meisel et al., (2004). "Human bone marrow stromal cells inhibit allogeneic T-cell responses by indoleamine 2,3-dioxygenase-mediated tryptophan degradation," Immunobiology, Blood, 103(12):4619-4621.
Melief, S., (2013). "Adipose Tissue-Derived Multipotent Stromal Cells Have a Higher Immunomodulatory Capacity Than Their Bone Marrow-Derived Counterparts," Stem Cells Translational Medicine, 2:455-463.
Mitchell et al., (2006). "Immunophenotype of Human Adipose-Derived Cells: Temporal Changes in Stromal-Associated and Stem Cell-Associated Markers," Stem Cells, 24:376-385.
Mizuno et al., (2003). "Mesengenic Potential and Future Clinical Perspective of Human Processed Lipoaspirate Cells," J Nippon Med Sch, 70:300-306.
Mizuno, H., (2003). "Versatility of Adipose Tissue as a Source of Stem Cells," J. Nippon Med. Sch., 70:428-431.
Muraglia et al., (2000). "Clonal mesenchymal progenitors from human bone marrow differentiate in vitro according to a hierarchical model," Journal of Cell Science, 113:1161-1166.
Newman et al. (2009). "Treatment of Inflammatory Diseases with Mesenchymal Stem Cells," Inflammation & Allergy—Drug Targets, 8:110-123.
Niehage et al. (2011). "The Cell Surface Proteome of Human Mesenchymal Stromal Cells" PLoS ONE 6(5): e20399. p. 1-10.
Peng, L. et al., (2008). "Comparative Analysis of Mesenchymal Stem Cells from bone Marrow, Cartilage, and Adipose Tissue," Stem Cells Develop, 17:761-774.
Polchert et al., (2008). "IFN-gamma activation of mesenchymal stem cells for treatment and prevention of graft versus host disease," Eu. J. Immunol., 38:1745-1755.

(56) References Cited

OTHER PUBLICATIONS

Romanov YA et al., (2005). "Mesenchymal Stem Cells from human Bone Marrow and Adipose Tissue: Isolation, Characterization, and Differentiation Potentialities," Bull Exp Biol Med, 140(1):138-143.
Salem et al., (2017). "Stem cell transplant in inflammatory bowel disease: a promising modality of treatment for a complicated disease course," Stem Cell Investigation, 4:1-5.
Shimizu et al., (2006). "Newly developed primary culture of rat visceral adipocytes and their in vitro characteristics", Cell Biology International, 30:381-388.
Sotiropoulou PA et al., (2006). "Interactions Between Human Mesenchymal Stem Cells and Natural Killer Cells," Stem Cells, 24:74-85.
Spaggiari GM et al., (2006). "Mesenchymal stem cell-natural killer cell interactions: evidence that activated NK cells are capable of killing MSCs, whereas MSCs can inhibit IL-2-induced NK-cell proliferation," Blood, 107:1484-1490.
Strem et al. (2005). "Multipotential differentiation of adipose tissue-derived stem cells," Keio J Med 54, (3):132-141.
Takeda and TiGenix Announce Publication in The Lancet of 24 Week Results of the Phase 3 Admire-CD Trial investigating Cx601 in the Treatment of Complex Perianal Fistulas in Patients with Crohn's Disease. Aug. 2, 2016. 5 pages.
Tigenix (2015). "Tigenix Living Medicines, Corporate Presentation, Feb. 2015," 40 pages.
Tigenix (2015). "Tigenix Living Medicines, Corporate Presentation, Mar. 2015," 39 pages.
Tigenix (2015). "Tigenix Living Medicines, Corporate Presentation, Oct. 2015," 40 pages.
Tigenix (2015). "Tigenix Living Medicines, Corporate Presentation, Sep. 2015," 41 pages.
Tigenix (2016). "Tigenix Living Medicines, Corporate Presentation, Jan. 2016," 39 pages.
Wakao et al. (2012). "Regenerative Effects of Mesenchymal Stem Cells: Contribution of Muse Cells, a Novel Pluripotent Stem Cell Type that Resides in Mesenchymal Cells," Cells, 1:1045-1060.
Wolf et al., (2009). "Regenerative capacity of intravenous autologous, allogeneic and human mesenchymal stem cells in the infarcted pig myocardium—complicated by myocardial tumor formation," Scandinavian Cardiovascular Journal, 43:39-45.
Zhang et al. (2017). "Preservation media, durations and cell concentrations of short-term storage affect key features of human adipose-derived mesenchymal stem cells for therapeutic application," PeerJ., 5:e3301. doi: 10.7717/peerj.3301. eCollection 2017.
Zhao et al., (2003). "Mechanisms of and perspectives on the mesenchymal stem cell in immunotherapy," J Lab Clin Med, 143(5):284-291.
Zuk, P. A., (2010). "The Adipose-derived Stem Cell: Looking Back and Looking Ahead," Molecular Biology of the Cell, 21:1783-1787.
Abedi et al. (2005). "Critical variables in the conversion of marrow cells to skeletal muscle," Blood, 106: 1488-1494.
Aggarwal et al., "Human mesenchymal stem cells modulate allogeneic immune cell responses," Blood, vol. 105, No. 4, 2005, pp. 1815-1822.
Bouffi et al., (2009). "Multipotent mesenchymal stromal cells and rheumatoid arthritis: risk or benefit?", Rheumatology, 2009, vol. 48, No. 10, pp. 1185-1189.
Cx611-0101, eASCs intravenous administration to refractory rheumatoid arthritis patients. ClinicalTrials.gov, U.S. National Library of Medicine, Aug. 13, 2012 [retrieved on Apr. 22, 2018]. Retrieved from the Internet: <URL:https://clinicaltrials.gov/ct2/show/NCT01663116>, 10 pages.
De Ugarte et al., (2003). "Differential expression of stem cell mobilization-associated molecules on multi-lineage cells from adipose tissue and bone marrow," Immunology Letters 89:267-270.
Deng et al., "Allogeneic bone marrow-derived flk-1 Sca-1 mesenchymal stem cells leads to stable mixed chimerism and donor-specific tolerance," Experimental Hematology, vol. 32, 2004, pp. 861-867.
Fouillard et al. (2003). "Engraftment of allogeneic mesenchymal stem cells in the bone marrow of a patient with severe idiopathic aplastic anemia improves stroma," Leukemia, 17: 474-476.
Gimble et al., (2003). "Adipose-derived adult stem cells: isolation, characterization, and differentiation potential," Cytotherapy, 5(5):362-369.
Gronthos et al., (2001). "Surface Protein Characterization of Human Adipose Tissue-Derived Stormal Cells," Journal of Cellular Physiology, vol. 189: 55-63.
Huang et al. (2010). "Differentiation of Allogeneic Mesenchymal Stem Cells Induces Immunogenicity and Limits Their Long-Term Benefits for Myocardial Repair," Circulation, 122: 2419-2429.
Kurozumi et al., (2004). "BDNF Gene-Modified Mesenchymal Stem Cell Promote Functional Recovery and Reduce Infarct Size in the Rat Middle Cerebral Artery Occlusion Model," Molecular Therapy, 9(2):189-197.
Le Blanc et al. (2003). "HLA expression and immunologic properties of differentiated and undifferentiated mesenchymal stem cells," Exp Hematol, 31(10):890-896.
Le Blanc et al., (2004). "Treatment of sever acute graft-versus-host disease with third party haploidentical mesenchymal stem cells," The Lancet, vol. 363, pp. 1439-1441.
Pittenger et al. (1999). "Multilineage potential of adult human mesenchymal stem cells," Science, 284(5411):143-147.
Rizk et al. (2016). "Heterogeneity in Studies of Mesenchymal Stromal Cells to Treat or Prevent Graft-versus-Host Disease: A Scoping Review of the Evidence," Biol Blood Marrow Trans, 22(8):1416-1423.
Search Report received for EP18152520, dated May 17, 2018, 11 pages.
Silva et al. (2005). "Mesenchymal Stem Cells Differentiate into an Endothelial Phenotype, Enhance Vascular Density, and Improve Heart Function in a Canine Chronic Ischemia Model," Circulation, 111:150-156.
Toma et al. (2002). "Human Mesenchymal Stem Cells Differentiate to a Cardiomyocyte Phenotype in the Adult Murine Heart," Circulation, 105:93-98.
Liu, et al. (2004) Am. J. Physiol. Heart Circ. Physiol. 287:H501-H511.†
Brady, et al. (1994) JVIB 4:525-529.†

\* cited by examiner
† cited by third party

FIG. 1

| Antigen | P1 | P3 | P4 | P6 | P7 | P9 |
|---|---|---|---|---|---|---|
| CD 34 (stem cell marker) | + | +/- | - | - | - | - |
| CD 90 (stem cell marker; fibroblasts) | + | ++ | ++ | +++ | +++ | +++ |
| c-Kit (stem cell marker) | + | + | ++ | +++ | +++ | +++ |
| Factor VIII (differentiation marker) | + | +/- | +/- | - | - | - |
| Alpha-actin (marker of vascular smooth muscle cells) | + | + | +/- | - | - | - |
| Vimentin (marker of mesoderm origin; mesenchymal cells) | +++ | +++ | +++ | +++ | +++ | +++ |
| Desmin (marker of mesoderm origin; muscle cells) | + | - | - | - | - | - |
| S-100 (marker of neuroectoderm origin) | | | | | | |
| Keratin (marker of ectoderm origin) | | | | | | |

FIG. 3

| Implant no. | Patient no. | Age (years) | Gender | Type of fistula | Passage no. | Culture time (days) | Cell number (x10⁶) | Outcome |
|---|---|---|---|---|---|---|---|---|
| 1 | 001 | 35 | F | Recto-vaginal | 1 | 6 | 6.1 | Healed |
| 2 | 002 | 40 | F | Enterocutaneous Middle line | 1 | 9 | 9.0 | Healed |
| 3 | 002 | 40 | F | Enterocutaneous Periumbilical | 1 | 7 | 8.0 | NA |
| NI | 003 | 36 | M | Perineal | 1 | NA | NI | NA |
| 4 | 002 | 40 | F | Recto-vaginal | 2 | 14 | 10.0 | Not Healed |
| 5 | 002 | 41 | F | Enterocutaneous Suprapubic | 2 | 8 | 3.5 | Healed |
| 6 | 001 | 37 | F | Rectovaginal | 1 | 12 | 20.0 | Healed |
| 7 | 004 | 36 | M | Enterocutaneous Right Lower Quadrant | 2 | 16 | 30.0 | Not Healed |
| 8 | 005 | 32 | M | Perineal | 2 | 31 | 20.0 | Healed |
| 9 | 002 | 41 | F | Enterocutaneous Right Lower Quadrant | 3 | 12 | 15.0 | Healed |

USE OF ADIPOSE TISSUE-DERIVED STROMAL STEM CELLS IN TREATING FISTULA

CROSS-REFERENCE TO RELATED APPLICATIONS

This application is a continuation of U.S. patent application Ser. No. 13/457,053 filed Apr. 26, 2012 (now abandoned), which is a continuation of U.S. patent application Ser. No. 11/167,061 filed Jun. 24, 2005 now abandoned), which is a continuation-in-part of U.S. patent application Ser. No. 11/065,461, filed on Feb. 25, 2005 now abandoned), and a continuation-in-part of U.S. patent application Ser. No. 11/056,241, filed on Feb. 14, 2005 (now abandoned), which claim priority to Spanish Application No. P200402355 filed Oct. 4, 2004 and Spanish Application No. P200402083 filed Aug. 25, 2004, the contents of which applications are herein specifically incorporated by reference in their entireties.

BACKGROUND OF THE INVENTION

Generally, a fistula is an abnormal connection or passageway between organs or vessels that normally do not connect. Fistulae can develop in various parts of the body. For example, types of fistulae, named for the areas of the body in which they occur, include anorectal fistula or fistula-in-ano or fecal fistula (between the rectum or other anorectal area and the skin surface), arteriovenous fistula or A-V fistula (between an artery and vein), biliary fistula (between the bile ducts to the skin surface, often caused by gallbladder surgery), cervical fistula (abnormal opening in the cervix), craniosinus fistula (between the intracranial space and a paranasal sinus), enteroenteral fistula (between two parts of the intestine), enterocutaneous fistula (between the intestine and the skin surface, namely from the duodenum or the jejunum or the ileum), enterovaginal fistula (between the intestine and the vagina), gastric fistula (between the stomach to the skin surface), metroperitoneal fistula (between the uterus and peritoneal cavity), perilymph fistula (a tear between the membranes between the middle and inner ears), pulmonary arteriovenous fistula (between an artery and vein of the lungs, resulting in shunting of blood), rectovaginal fistula (between the rectum and the vagina), umbilical fistula (between the umbilicus and gut), tracheoesophageal fistula (between the breathing and the feeding tubes) and vesicovaginal fistula (between the bladder and the vagina). Causes of fistulae include trauma, complications from medical treatment and disease.

Treatment for fistulae varies depending on the cause and extent of the fistula, but generally involves surgical intervention. Various surgical procedures are commonly used, most commonly fistulotomy, placement of a seton (a cord that is passed through the path of the fistula to keep it open for draining), or an endorectal flap procedure (where healthy tissue is pulled over the internal side of the fistula to keep feces or other material from reinfecting the channel). Surgery for anorectal fistulae is not without side effects, including recurrence, reinfection, and incontinence.

Inflammatory bowel diseases, such as Crohn's disease and ulcerative colitis, are the leading causes of anorectal, enteroenteral, and enterocutaneous fistulae. The reported incidence of fistula in Crohn's disease ranges from 17% to 50%. Management of fistulae in patients with Crohn's disease continues to present an extremely challenging problem since many such fistulae do not respond to available treatments. Such fistulae and their recurrence are a very distressing complication that significantly reduces the quality of life of affected patients. Recent improvements in medical treatment (e.g., treatment with Infliximab) and expert surgical management have decreased the need for complicated surgery. However, many patients are not cured. Failure of fistulae to heal is probably due to the suboptimal quality of tissues that have been affected by Crohn's disease. Indeed, Crohn's fistulae provide a model system for wound healing under some of the worst possible conditions.

Another leading cause of fistulae is trauma, e.g. by rape, or by injuries sustained during childbirth, to the tissues of the vagina and the bladder and/or rectum leading to rectovaginal fistula and vesicovaginal fistula. Every year approximately 100,000 women across the developing world sustain such fistulae (also known as obstetric fistulae) during obstructed labor. During obstructed labor, the pressure of the baby's head against the mother's pelvis cuts off blood supply to delicate tissues in the region. The dead tissue falls away and the woman is left with a vesicovaginal fistula and sometimes a rectovaginal fistula. This hole results in permanent incontinence of urine and/or feces. The United Nations Population Fund (UNFPA) estimates the world's population of obstetric fistula sufferers at more than two million. This calculation could be a significant underestimate. Success rates for primary surgical repair range from 88 to 93 percent but decrease with successive attempts. Thus, a significant percentage of women have obstetrical fistulae that cannot be repaired surgically.

New therapies for fistulae are needed.

SUMMARY OF THE INVENTION

Provided herein, among other things, are novel adipose tissue-derived stromal stem cell-containing compositions. The adipose tissue-derived stromal stem cell-containing compositions described herein have a distinct phenotype and exhibit greater homogeneity of phenotype than previously described adipose tissue-derived stromal stem cell compositions, thus making them more suitable for use in treating fistulae and wounds than previously described compositions. The adipose tissue-derived stromal stem cell-containing compositions may be formulated with solutions or other substances to serve as pharmaceuticals or medical devices, e.g., as sutures or adhesives. Further, provided are novel methods of treating fistulae and wounds using adipose tissue-derived stromal stem cells, as well as kits for the practice of the same.

These embodiments of the present invention, other embodiments, and their features and characteristics will be apparent from the description, drawings, and claims that follow.

BRIEF DESCRIPTION OF THE FIGURES

FIG. 1 depicts the results of characterization of cells isolated by the methods of Example 1 by immunofluorescence staining. The frequency of immunopositive cells is indicated as follows: −, less than 5%; +/−, 6-15%; +, 16-50%; ++, 51-85%; and +++, 86-100%. P, Passage number.

FIG. 3 summarizes the clinical results obtained using certain methods and compositions of the invention. F, Female; M, male; NI, No implant; NA, Not analyzed.

DETAILED DESCRIPTION OF THE INVENTION

1. Definitions

Figure 2:
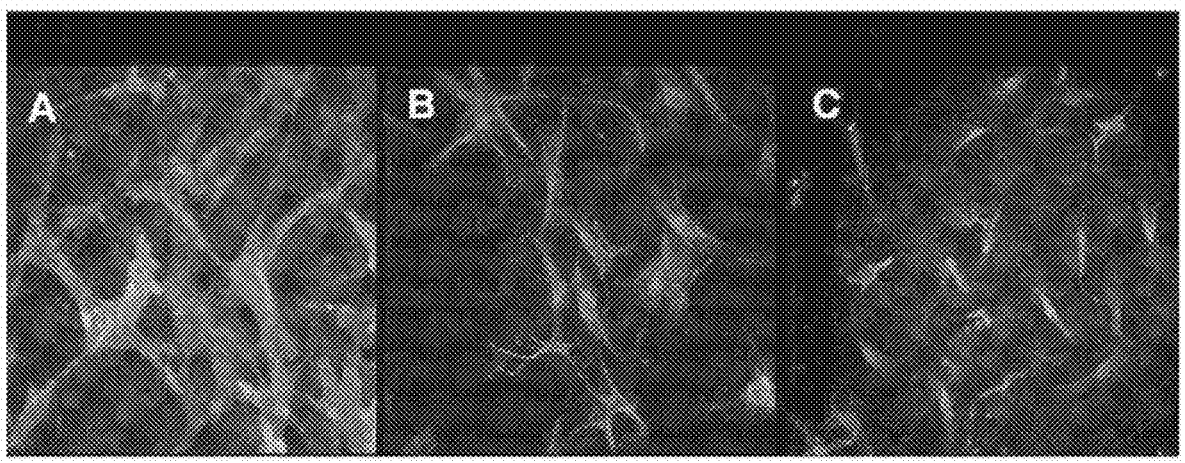
FIG. 2 depicts indirect immunofluorescence characterization of adipose tissue-derived stromal stem cells. Cells from patient #001 were passaged 6 cells subsequent to implant no. 6. Blue color indicates DAPI-stained nuclei. (A) CD90; (B) c-Kit; and (C) vimentin.

As used herein, the following terms and phrases shall have the meanings set forth below. Unless defined otherwise, all technical and scientific terms used herein have the same meaning as commonly understood to one of ordinary skill in the art to which this invention belongs.

The articles "a" and "an" refer to one or to more than one (i.e., to at least one) of the grammatical object of the article. By way of example, "an element" means one element or more than one element.

By "adipose tissue" is meant any fat tissue. The adipose tissue may be brown or white adipose tissue, derived from subcutaneous, omental/visceral, mammary, gonadal, or other adipose tissue site. Preferably, the adipose tissue is subcutaneous white adipose tissue. Such cells may comprise a primary cell culture or an immortalized cell line. The adipose tissue may be from any organism having fat tissue. Preferably, the adipose tissue is mammalian, most preferably the adipose tissue is human. A convenient source of adipose tissue is from liposuction surgery, however, the source of adipose tissue or the method of isolation of adipose tissue is not critical to the invention. If stromal cells are desired for autologous transplantation into a subject, the adipose tissue will be isolated from that subject.

"Adipose tissue-derived stromal stem cells" refers to mesemchymal stern cells that originate from adipose tissue.

The term "adhesive" refers to any substance that unites or bonds surfaces together; e.g., a glue.

The term "cellular composition" refers to a preparation of cells, which preparation may include, in addition to the cells, non-cellular components such as cell culture media, e.g. proteins, amino acids, nucleic acids, nucleotides, co-enzyme, anti-oxidants, metals and the like. Furthermore, the cellular composition can have components which do not affect the growth or viability of the cellular component but which are used to provide the cells in a particular format, e.g., as polymeric matrix for encapsulation or a pharmaceutical preparation.

The term "culture" refers to any growth of cells, organisms, multicellular entities, or tissue in a medium. The term "culturing" refers to any method of achieving such growth, and may comprise multiple steps. The term "further culturing" refers to culturing a cell, organism, multicellular entity, or tissue to a certain stage of growth, then using another culturing method to bring said cell, organism, multicellular entity, or tissue to another stage of growth. A "cell culture" refers to a growth of cells in vitro. In such a culture, the cells proliferate, but they do not organize into tissue per se. A "tissue culture" refers to the maintenance or growth of tissue, e.g., explants of organ primordial or of an adult organ in vitro so as to preserve its architecture and function. A "monolayer culture" refers to a culture in which cells multiply in a suitable medium while mainly attached to each other and to a substrate. Furthermore, a "suspension culture" refers to a culture in which cells multiply while suspended in a suitable medium. Likewise, a "continuous flow culture" refers to the cultivation of cells or explants in a continuous flow of fresh medium to maintain cell growth, e.g. viability. The term "conditioned media" refers to the supernatant, e.g. free of the cultured cells/tissue, resulting after a period of time in contact with the cultured cells such that the media has been altered to include certain paracrine and/or autocrine factors produced by the cells and secreted into the culture. A "confluent culture" is a cell culture in which all the cells are in contact and thus the entire surface of the culture vessel is covered, and implies that the cells have also reached their maximum density, though confluence does not necessarily mean that division will cease or that the population will not increase in size.

The term "culture medium" or "medium" is recognized in the art, and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. Similarly, a powder mixture that when mixed with water or other liquid becomes suitable for cell culture may be termed a "powdered medium". "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. A "medium suitable for growth of a high density culture" is any medium that allows a cell culture to reach an OD600 of 3 or greater when other conditions (such as temperature and oxygen transfer rate) permit such growth. The term "basal medium" refers to a medium which promotes the growth of many types of microorganisms which do not require any special nutrient supplements. Most basal media generally comprise of four basic chemical groups: amino acids, carbohydrates, inorganic salts, and vitamins. A basal medium generally serves as the basis for a more complex medium, to which supplements such as serum, buffers, growth factors, lipids, and the like are added. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, McCoy's 5A, Dulbecco's MEM/F-I 2, RPMI 1640, and Iscove's Modified Dulbecco's Medium (IMDM).

The terms "comprise" and "comprising" are used in the inclusive, open sense, meaning that additional elements may be included.

The term "differentiation" refers to the formation of cells expressing markers known to be associated with cells that are more specialized and closer to becoming terminally differentiated cells incapable of further division or differentiation. For example, in a pancreatic context, differentiation can be seen in the production of islet-like cell clusters containing an increased proportion of beta-epithelial cells that produce increased amounts of insulin. The terms "further" or "greater" differentiation refers to cells that are more specialized and closer to becoming terminally differentiated cells incapable of further division or differentiation than the cells from which they were cultured. The term "final differentiation" refers to cells that have become terminally differentiated cells incapable of further division or differentiation.

The term "fistula" refers to any abnormal passage or communication or connection, usually between two internal organs or leading from an internal organ to the surface of the body. Examples of fistulae include, but are not limited to, anorectal fistula or fistula-in-ano or fecal fistula, arteriovenous fistula or A-V fistula, biliary fistula, cervical fistula, craniosinus fistula, enteroenteral fistula, enterocutaneous fistula, enterovaginal fistula, gastric fistula, metroperitoneal fistula perilymph, pulmonary arteriovenous fistula, rectovaginal fistula, umbilical fistula, tracheoesophageal fistula and vesicovaginal fistula.

The term "including" is used herein to mean "including but not limited to". "Including" and "including but not limited to" are used interchangeably.

"Marker" refers to a biological molecule whose presence, concentration, activity, or phosphorylation state may be detected and used to identify the phenotype of a cell.

A "patch" is a dressing or covering applied to cover or protect a wound or other sore.

A "patient", "subject" or "host" to be treated by the subject method may mean either a human or non-human animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. The term "phenotype" refers to the observable characteristics of a cell, such as size, morphology, protein expression, etc.

The term "progenitor cell" refers to a cell that has the capacity to create progeny that are more differentiated than itself. For example, the term may refer to an undifferentiated cell or cell differentiated to an extent short of final differentiation which is capable of proliferation and giving rise to more progenitor cells having the ability to generate a large number of mother cells that can in turn give rise to differentiated or differentiable daughter cells. In a preferred embodiment, the term progenitor cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. By this definition, stem cells may also be progenitor cells, as well as the more immediate precursors to terminally differentiated cells.

"Proliferation" refers to an increase in cell number. "Proliferating" and "proliferation" refer to cells undergoing mitosis.

As used herein, the term "solution" includes a pharmaceutically acceptable carrier or diluent in which the cells of the invention remain viable.

The term "substantially pure", with respect to adipose tissue-derived stem cell populations, refers to a population of adipose tissue-derived stem cell cells that is at least about 75%, preferably at least about 85%, more preferably at least about 90%, and most preferably at least about 95% pure, with respect to adipose tissue-derived stromal stem cells making up a total cell population. Recast, the term "substantially pure" refers to a population of adipose tissue-derived stromal stem cells of the present invention that contain fewer than about 20%, more preferably fewer than about 10%, most preferably fewer than about 5%, of lineage committed cells in the original unamplified and isolated population prior to subsequent culturing and amplification.

"Support" as used herein refers to any device or material that may serve as a foundation or matrix for the growth of adipose tissue-derived stromal stem cells.

The term "suture" refers to a thread or fiber or other fastening material that can be used to sew a wound together.

The term "treating" as used herein refers to repairing a fistula or wound, as well as preventing a fistula or wound from worsening or recurring.

"Therapeutic agent" or "therapeutic" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents are known in the art and may be identified by their effects. Certain therapeutic agents are capable of regulating cell proliferation and differentiation. Examples include chemotherapeutic nucleotides, drugs, hormones, non-specific (non-antibody) proteins, oligonucleotides (e.g., antisense oligonucleotides that bind to a target nucleic acid sequence (e.g., mRNA sequence)), peptides, and peptidomimetics.

A "wound" is an injury or damage to tissue, caused by physical means, causing disruption of normal continuity of the tissue.

2. Novel Adipose Tissue-Derived Stromal Stem Cell-Containing Compositions

In one aspect, the invention relates to adipose tissue-derived stromal stem cell-containing compositions with certain characteristics, such as a particular phenotype. For example, the adipose tissue-derived stromal stem cells in a cellular composition of the invention may be characterized by cell surface marker expression, size, glucose consumption, lactate production, and cell yield/viability. Yet another aspect of the present invention concerns adipose tissue-derived stromal stem cell-containing compositions which include, as a cellular component, substantially pure preparations of adipose tissue-derived stromal stem cells having a particular phenotype, or the progeny thereof. Adipose tissue-derived stromal stem cell-containing compositions of the present invention include not only substantially pure populations of the progenitor cells, but can also include cell culture components, e.g., culture media including amino acids, metals, coenzyme factors, as well as small populations of other stromal cells, e.g., some of which may arise by subsequent differentiation of cells of the invention. Furthermore, other non-cellular components can include those which render the cellular component suitable for support under particular circumstances, e.g., implantation, e.g., continuous culture, or suitable for use as a biomaterial or pharmaceutical composition.

In certain embodiments, the adipose tissue-derived stromal stem cell-containing compositions are produced through the culture methods described in Section 4 and the Exemplification.

In one embodiment, provided is an adipose tissue-derived stromal stem cell-containing composition, wherein at least about 50%, at least about 60%, at least about 70%, at least about 80%, at least about 85%, at least about 90%, at least about 95% or preferably at least about 96%, 97%, 98% or 99% of the stem cells express the CD9, CD10, CD13, CD29, CD44, CD49A, CD51, CD54, CD55, CD58, CD59, CD90 and/or CD105 markers. In certain embodiments of the adipose tissue-derived stromal stem cell-containing compositions, fewer than about 15%, about 10%, about 5%, and preferably about 4%, 3%, 2% or 1% of the stem cells express the CD34, CD11b, CD14, CD15, CD16, CD31, CD34, CD45, CD49f, CD102, CD104, CD106 and/or CD133 markers.

In another embodiment, provided is an adipose tissue-derived stromal stem cell-containing composition, wherein at least about 50%, at least about 60%, at least about 70%, at least about 80%, at least about 85%, at least about 90%, at least about 95% or preferably at least about 96%, 97%, 98% or 99% of the stem cells express the c-Kit, vimentin and/or CD90 markers. In certain embodiments of the adipose tissue-derived stromal stem cell-containing compositions, fewer than about 15%, about 10%, about 5%, and preferably about 4%, 3%, 2% or 1% of the stem cells express the CD34, Factor VIII, alpha-actin, desmin, S-100 and/or keratin markers. Also provided is an adipose tissue-derived stromal stem cell population that express the c-Kit, vimentin and CD90 markers and does not express the CD34, Factor VIII, alpha-actin, desmin, S-100 and keratin markers.

The phenotypic characterization of a cell population by surface markers can be performed either by individual staining of the cells (flow cytometry) or by making histological cuts of the population in situ, done in accordance with normal methods. The determination of the profile of expression of surface markers by antibodies, immunophenotype characterization, may be direct, using a labeled antibody or indirect, using a second labeled antibody against the primary specific antibody of the cell marker, thus achieving signal amplification. On the other hand, the presence or absence of binding to the antibody may be determined by different methods that include but are not limited to immunofluorescence microscopy and radiography. Similarly, it is possible to carry out the monitoring of the levels of binding of the antibody by flow cytometry, a technique that allows the levels of fluorochrome to be correlated with the quantity of antigens present on the cell surface bound specifically to the labeled antibodies. The differential expression of a series of surface markers on a cell population provides a method for identification and isolation of said population.

In certain embodiments, the adipose tissue-derived stromal stem cell-containing compositions are suspensions of adipose tissue-derived stromal stem cells in various solutions or materials, e.g. for use as pharmaceuticals or biomaterials, as described in more detail below. In one embodiment, the cellular composition comprises a suspension of the subject adipose tissue-derived stromal stem cells in Ringer's solution and HSA. In another embodiment, the cellular composition comprises a suspension of the subject adipose tissue-derived stromal stem cells in a material, such as a polymer, glue, gel, etc. Such suspensions may be prepared, for example, by sedimenting out the subject adipose tissue-derived stromal stem cells from the culture medium and re-suspending them in the desired solution or material. The cells may be sedimented and/or changed out of the culture medium, for example, by centrifugation, filtration, ultrafiltration, etc.

The concentration of the subject adipose tissue-derived stromal stem cells in the subject adipose tissue-derived stromal stem cell-containing compositions may be at least about $5 \times 10^6$ cells/mL, at least about $10 \times 10^6$ cells/mL, at least about $20 \times 10^6$ cells/mL, at least about $30 \times 10^6$ cells/mL, or at least about $40 \times 10^6$ cells/mL.

Accordingly, another aspect of the present invention pertains to the progeny of the subject adipose tissue-derived stromal stem cells, e.g. those cells which have been derived from the adipose tissue-derived stromal stem cells. Such progeny can include subsequent generations of adipose tissue-derived stromal stem cells, as well as lineage committed cells generated by inducing differentiation of the subject adipose tissue-derived stromal stem cells after their isolation from the explant, e.g., induced in vitro. In certain embodiments, the progeny cells are obtained after about 2, about 3, about 4, about 5, about 6, about 7, about 8, about 9, or about 10 passages from the parental population. However, the progeny cells may be obtained after any number of passages from the parental population.

In certain embodiments, the adipose tissue-derived stromal stem cell-containing compositions of the invention will be provided as part of a pharmaceutical preparation, e.g., a sterile, free of the presence of unwanted virus, bacteria and other pathogens, as well as pyrogen-free preparation. That is, for human administration, the subject compositions should meet sterility, pyrogenicity as well as general safety and purity standards as required by FDA Office of Biologics standards.

In certain embodiments, such adipose tissue-derived stromal stem cell-containing compositions can be used for transplantation into animals, preferably mammals, and even more preferably humans. The cells can be preferably autologous, but also allogeneic or xenogeneic with respect to the transplantation host. Because of difficulties in obtaining sufficient autologous stem cells, adipose tissue-derived stromal stem cell from allogenic donor could constitute a valuable alternative source of stem cells for therapeutic use. It is known in the art that bone marrow stromal stem cells and adipose tissue-derived stromal cells did not provoke a response of allogenic lymphocytes in vitro and consequently, allogenic adipose tissue-derived stromal stem cells derived from a donor could be theorically used for any patient, irrespective of MHC incompatibility.

Methods of administering the adipose tissue-derived stromal stem cell-containing compositions to subjects, particularly human subjects, which are described in detail herein, include injection or implantation of the cells into target sites in the subjects, the cells can be inserted into a delivery device which facilitates introduction by, injection or implantation, of the cells into the subjects. Such delivery devices include tubes, e.g., catheters, for injecting cells and fluids into the body of a recipient subject. In a preferred embodiment, the tubes additionally have a needle, e.g., a syringe, through which the adipose tissue-derived stromal stem cell-containing compositions can be introduced into the subject at a desired location. The adipose tissue-derived stromal stem cell-containing compositions can be inserted into such a delivery device, e.g., a syringe, in different forms. For example, the adipose tissue-derived stromal stem cell-containing compositions include compositions of adipose tissue-derived stromal stem cells that are suspended in a solution or embedded in a support matrix when contained in such a delivery device.

Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions that are adipose tissue-derived stromal stem cell compositions of the invention can be prepared by incorporating adipose tissue-derived stromal stem cells as described herein in a pharmaceutically acceptable carrier or diluent and, as required, other ingredients enumerated above, followed by filtered sterilization.

Some examples of materials and solutions which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

In certain embodiments, the adipose tissue-derived stromal stem cell-containing compositions further comprise an adhesive. In certain embodiments, the adhesive is a fibrin-based adhesive, such as a fibrin gel or fibrin glue or fibrin-based polymer or adhesive, or other tissue adhesive or surgical glue, such as, for example cyanoacrylate, collagen, thrombin, and polyethylene glycol. Other materials that may be used include but are not limited to calcium alginate, agarose, types I, II, IV or other collagen isoform, poly-lactic/poly-glycolic acid, hyaluronate derivatives or other materials (Perka C. et al. (2000) J. Biomed. Mater. Res. 49:305-311; Sechriest V F. et al. (2000) J. Biomed. Mater. Res. 49:534-541; Chu C R et al. (1995) J. Biomed. Mater. Res. 29:1147-1154; Hendrickson D A et al. (1994) Orthop. Res. 12:485-497). In other embodiments, the adhesive is a liquid bandage, wherein adipose tissue-derived stromal stem cell-containing compositions of the method are mixed with the liquid bandage material. A "liquid bandage" is a solution comprising a compound, e.g. a polymeric material, which is applied to a wound with a spray or a brush, followed by removing the solvent by vaporization to provide a protective film on the wound.

Provided herein are also methods for preparing adipose tissue-derived stromal stem cell-containing compositions comprising compounds or materials for use in repairing fistula or wounds. In one embodiment, a method of preparing such materials comprises suspending the adipose tissue-derived stromal stem cells of a subject cellular composition with the material. In one embodiment, the adipose tissue-derived stromal stem cells are sedimented out of the culture medium and re-suspended in a fibrin glue or gel. Fibrin glues and gels and other fibrin-based polymers and adhesives are well-known in the art and are commercially available. For example, a commercially available fibrin glue kit is the TISSUCOL® Duo 2.0, and other commercially available fibrin sealants include CROSSEAL®, TISSEEL VH FIBRIN SEALANT®, and the like.

The adipose tissue-derived stromal stem cell-containing compositions of the invention may also be used to coat a support, e.g. a medical device. For example, the support may be a suture, thread, meniscus repair device, rivet, tack, staple, screw, bone plate, bone plating system, surgical mesh, patch, e.g. a repair patch, cardiovascular patch, or pericardial patch, sling, orthopedic pin, adhesion barrier, stent, guided tissue repair/regeneration device, articular cartilage repair device, nerve guide, tendon repair device, atrial septal defect repair device, bulking or tilling agent, vein valve, bone marrow scaffold, meniscus regeneration device, ligament and tendon graft, ocular cell implant, spinal fusion cage, skin substitute, dural substitute, bone graft substitute, bone dowel, wound dressing, glue, polymer or hemostat.

Supports into which the adipose tissue-derived stromal stem cell-containing compositions can be incorporated or embedded or onto which the adipose tissue-derived stromal stem cell-containing compositions may be coated include matrices which are recipient-compatible and which degrade into products which are not harmful to the recipient. Natural and/or synthetic biodegradable matrices are examples of such matrices. Natural biodegradable matrices include plasma clots, e.g., derived from a mammal, and collagen matrices. Synthetic biodegradable matrices include synthetic polymers such as polyanhydrides, polyorthoesters, and polylactic acid. Other examples of synthetic polymers and methods of incorporating or embedding cells into these matrices are known in the art. See e.g., U.S. Pat. Nos. 4,298,002 and 5,308,701. These matrices provide support and protection for the fragile cells in vivo.

The support may be coated with cells in any way as known to one of skill in the art, e.g. by soaking, spraying, painting, imprinting, etc.

In one embodiment, the support is a suture, staple, absorbable thread, non-absorbable thread, natural thread, synthetic thread, monofilament thread or multifilament thread (also called braids). Preferred methods of preparing sutures and other supports used to close wounds coated with adipose tissue-derived stromal stem cells are disclosed in U.S. patent application Ser. No. 11/056,241 "Biomaterial for Suturing", filed Feb. 14, 2005, which application is incorporated by reference in its entirety. The adipose tissue-derived stromal stem cell-containing compositions disclosed herein represent novel compositions that may be used with the methods disclosed in U.S. patent application Ser. No. 11/056,241.

Further, in any of the adipose-tissue derived stromal stem cell-containing compositions, at least one therapeutic agent may be incorporated into the composition. For example, a composition may contain an analgesic, to aid in treating inflammation or pain at the site of the fistula or wound, or an anti-infective agent to prevent infection of the site treated with the composition.

More specifically, non-limiting examples of useful therapeutic agents include the following therapeutic categories: analgesics, such as nonsteroidal anti-inflammatory drugs, opiate agonists and salicylates; anti-infective agents, such as antihelmintics, antianaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, anti-inflammatory agents, corticosteroid anti-inflammatory agents, antipruritics/local anesthetics, topical anti-infectives, antifungal topical anti-infectives, antiviral topical anti-infectives; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hormones and hormone modifiers, such as abortifacients, adrenal agents, cortico steroid adrenal agents, androgens, anti-androgens, immunobiologic agents, such as immunoglobulins, immunosuppressives, toxoids, and vaccines; local anesthetics, such as amide local anesthetics and ester local anesthetics: musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, minerals; and vitamins, such as vitamin A, vitamin B, vitamin C, vitamin D, vitamin E, and vitamin K.

Preferred classes of useful therapeutic agents from the above categories include: (1) analgesics in general, such as lidocaine or derivatives thereof, and nonsteroidal anti-inflammatory drugs (NSAIDs) analgesics, including diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) anti-infective agents, such as mupirocin; (6) antianaerobic anti-infectives, such as chloramphenicol and clindamycin; (7) antifungal antibiotic anti-infectives, such as amphotericin b, clotrimazole, fluconazole, and ketoconazole; (8) macrolide antibiotic anti-infectives, such as azithromycin and erythromycin; (9) miscellaneous β-lactam antibiotic anti-infectives, such as aztreonam and imipenem; (10) penicillin antibiotic anti-infectives, such as nafcillin, oxacillin, penicillin G, and penicillin V; (11) quinolone antibiotic anti-infectives, such as ciprofloxacin and norfloxacin; (12) tetracycline antibiotic anti-infectives, such as doxycycline, minocycline, and tetracycline; (13) antituberculosis antimycobacterial anti-infectives such as isoniazid (INH), and rifampin; (14) antiprotozoal anti-infectives, such as atovaquone and dapsone; (15) antimalarial antiprotozoal anti-infectives, such as chloroquine and pyrimethamine; (16) anti-retroviral anti-infectives, such as ritonavir and zidovudine; (17) antiviral anti-infective agents, such as acyclovir, ganciclovir, interferon alfa, and rimantadine; (18) antifungal topical anti-infectives, such as amphotericin B, clotrimazole, miconazole, and nystatin; (19) antiviral topical anti-infectives, such as acyclovir; (20) electrolytic and renal agents, such as lactulose; (21) loop diuretics, such as furosemide; (22) potassium-sparing diuretics, such as triamterene; (23) thiazide diuretics, such as hydrochlorothiazide (HCTZ); (24) uricosuric agents, such as probenecid; (25) enzymes such as RNase and DNase; (26) antiemetics, such as prochlorperazine; (27) salicylate gastrointestinal anti-inflammatory agents, such as sulfasalazine; (28) gastric acid-pump inhibitor anti-ulcer agents, such as omeprazole; (29) $H_2$-blocker anti-ulcer agents, such as cimetidine, famotidine, nizatidine, and ranitidine; (30) digestants, such as pancrelipase; (31) prokinetic agents, such as erythromycin; (32) ester local anesthetics, such as benzocaine and procaine; (33) musculoskeletal corticosteroid anti-inflammatory agents, such as beclomethasone, betamethasone, cortisone, dexamethasone, hydrocortisone, and prednisone; (34) musculoskeletal anti-inflammatory immunosuppressives, such as azathioprine, cyclophosphamide, and methotrexate; (35) musculoskeletal nonsteroidal anti-inflammatory drugs (NSAIDs), such as diclofenac, ibuprofen, ketoprofen, ketorlac, and naproxen; (36) minerals, such as iron, calcium, and magnesium; (37) vitamin B compounds, such as cyanocobalamin (vitamin $B_{12}$) and niacin (vitamin $B_3$); (38) vitamin C compounds, such as ascorbic acid; and (39) vitamin D compounds, such as calcitriol.

In certain embodiments, the therapeutic agent may be a growth factor or other molecule that affects cell differentiation and/or proliferation. Growth factors that induce final differentiation states are well-known in the art, and may be selected from any such factor that has been shown to induce a final differentiation state. Growth factors for use in methods described herein may, in certain embodiments, be variants or fragments of a naturally-occurring growth factor. For example, a variant may be generated by making conservative amino acid changes and testing the resulting variant in one of the functional assays described above or another functional assay known in the art. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As those skilled in the art will appreciate, variants or fragments of polypeptide growth factors can be generated using conventional techniques, such as mutagenesis, including creating discrete point mutation(s), or by truncation. For instance, mutation can give rise to variants which retain substantially the same, or merely a subset, of the biological activity of a polypeptide growth factor from which it was derived.

3. Methods of Preparing Novel Adipose Tissue-Derived Stromal Stem Cell-Containing Compositions Methods of preparing the adipose tissue-derived stromal stem cells comprising the above-described adipose tissue-derived stromal stem cell-containing compositions are also provided. In one embodiment, a method comprises: (a) collecting adipose tissue from a subject; (b) obtaining a cell suspension by enzymatic digestion; (c) sedimenting the cell suspension and resuspending the cells in a culture medium; (d) culturing of the cells for at least about 10 days; and (g) expanding the cells for at least two culture passages.

Preferably, the adipose tissue-derived stromal stem cells are isolated from the adipose tissue of the subject into which the final adipose tissue-derived stromal stem cell-containing compositions are to be introduced. However, the stromal stem cells may also be isolated from any organism of the same or different species as the subject. Any organism with adipose tissue can be a potential candidate. Preferably, the organism is mammalian, most preferably the organism is human.

In certain embodiments, the cells are cultured for at least about 15, at least about 20 days, at least about 25 days, or at least about 30 days. It is preferable that cells are expanded in culture longer to improve the homogeneity of the cell phenotype in the cell population.

In certain embodiments, the cells are expanded in culture for at least three culture passages or "passaged at least three times." In other embodiments, the cells are passaged at least four times, at least five times, at least six times, at least seven times, at least eight times, at least nine times, or at least ten times. It is preferable that cells are passaged more than three times to improve the homogeneity of the cell phenotype in the cell population. Indeed, the cells may be expanded in culture indefinitely so long as the homogeneity of the cell phenotype is improved and differential capacity is maintained.

Cells may be cultured by any technique known in the art for the culturing of stem cells. A discussion of various culture techniques, as well as their scale-up, may be found in Freshney, R. I., *Culture of Animal Cells: A Manual of Basic Technique*, 4th Edition, Wiley-Liss 2000. In certain embodiments, the cells are cultured by monolayer culture. In one embodiment, the cells are cultured and passaged as described in Example 1 below.

Any medium capable of supporting stromal cells in tissue culture may be used. Media formulations that will support the growth of fibroblasts include, but are not limited to, Dulbecco's Modified Eagle's Medium (DMEM), alpha modified Minimal Essential Medium (.alpha.MEM), and Roswell Park Memorial Institute Media 1640 (RPMI Media 1640) and the like. Typically, 0 to 20% Fetal Bovine Serum (FBS) or 1-20% horse serum will be added to the above media in order to support the growth of stromal cells and/or chondrocytes. However, a defined medium could be used if the necessary growth factors, cytokines, and hormones in FBS for stromal cells and chondrocytes are identified and provided at appropriate concentrations in the growth medium. Media useful in the methods of the invention may contain one or more compounds of interest, including, but not limited to antibiotics mitogenic or differentiative compounds for stromal cells. The cells will be grown at temperatures between 31 degree C. to 37 degree C. in a humidified incubator. The carbon dioxide content will be maintained between 2% to 10% and the oxygen content between 1% and 22%. Cells may remain in this environment for periods of up to 4 weeks.

Antibiotics which can supplemented into the medium include, but are not limited to penicillin and streptomycin. The concentration of penicillin in the chemically defined culture medium is about 10 to about 200 units per ml. The concentration of streptomycin in the chemically defined culture medium is about 10 to about 200 ug/ml.

The adipose tissue derived stromal stem cells may be stably or transiently transfected or transduced with a nucleic acid of interest using a plasmid, viral or alternative vector strategy. Nucleic acids of interest include, but are not limited to, those encoding gene products which enhance the production of extracellular matrix components found in the tissue type to be repaired, e.g. intestinal wall or vaginal wall.

The transduction of viral vectors carrying regulatory genes into the stromal stem cells can be performed with viral vectors (adenovirus, retrovirus, adeno-associated virus, or other vector) purified by cesium chloride banding or other method at a multiplicity of infection (viral units:cell) of between 10:1 to 2000:1. Cells will be exposed to the virus in serum free or serum-containing medium in the absence or presence of a cationic detergent such as polyethyleneimine or LIPOFECTAMINE™ for a period of 1 hour to 24 hours (Byk T. et al. (1998) Human Gene Therapy 9:2493-2502; Sommer B. et al. (1999) Calcif. Tissue Int. 64:45-49).

Other suitable methods for transferring vectors or plasmids into stem cells include lipid/DNA complexes, such as those described in U.S. Pat. Nos. 5,578,475; 5,627,175; 5,705,308; 5,744,335; 5,976,567; 6,020,202; and 6,051,429. Suitable reagents include LIPOFECTAMINE™, a 3:1 (w/w) liposome formulation of the poly-cationic lipid 2,3-dioleyloxy-N-[2(sperminecarbox-amido)ethyl]-N,N-dimethyl-1-propanaminium trifluoroacetate (DOSPA) (Chemical Abstracts Registry name: N-[2-(2,5-bis[(3-aminopropyl)amino]-1-oxpentyl}amino) ethyl]-N,N-dimethyl-2,3-bis(9- octadecenyloxy)-1-propanaminium trifluoroacetate), and the neutral lipid dioleoyl phosphatidylethanolamine (DOPE) in membrane filtered water. Exemplary is the formulation LIPOFECTAMINE 2000™ (available from Gibco/Life Technologies #11668019). Other reagents include: FUGENE™ 6 Transfection Reagent (a blend of lipids in non-liposomal form and other compounds in 80% ethanol, obtainable from Roche Diagnostics Corp. #1814443); and LIPOTAXI™ transfection reagent (a lipid formulation from Invitrogen Corp., #204110). Transfection of stem cells can be performed by electroporation, e.g., as described in M. L Roach and J. D. McNeish (2002) Methods in Mol. Biol. 185:1. Suitable viral vector systems for producing stem cells with stable genetic alterations may be based on adenoviruses and retroviruses, and may be prepared using commercially available virus components.

The transfection of plasmid vectors carrying regulatory genes into the stem stromal cells can be introduced into the cells in monolayer cultures by use of calcium phosphate DNA precipitation or cationic detergent methods (LIPOFECTAMINE™, DOTAP) or in three dimensional cultures by incorporation of the plasmid DNA vectors directly into the biocompatible polymer (Bonadio J. et al. (1999) Nat. Med. 5:753-759).

For the tracking and detection of functional proteins encoded by these genes, the viral or plasmid DNA vectors will contain a readily detectable marker gene, such as the green fluorescent protein or beta-galactosidase enzyme, both of which can be tracked by histochemical means.

4. Methods of Treating Fistulae and Wounds

Another aspect of the invention concerns a novel method for using adipose tissue-derived stromal stem cells in treating fistulae and wounds. In preferred embodiments, the adipose tissue-derived stromal stem cells are derived from the adipose tissue of the subject to be treated. In other preferred embodiments, the adipose tissue-derived stromal stem cells comprise a adipose tissue-derived stromal stem cell-containing composition described herein. However, other preparations of adipose tissue-derived stromal stem cells may be used in the methods described herein, e.g. such as those described in U.S. Pat. Nos. 6,777,231 and 6,555,374 and U.S. patent application Ser. No. 11/065,461 "Identification and Isolation of Multipotent Cells From Non-Osteochondral Mesenchymal Tissue", filed on Feb. 25, 2005.

In one embodiment, a method of treating a fistula in a subject comprises: (a) closing the internal hole with a suture and (b) delivering at least about $10\times10^6$, at least about $20\times10^6$, at least about $30\times10^6$, or at least about $40\times10^6$ adipose tissue-derived stromal stem cells, e.g., in an adipose tissue-derived stromal stem cell-containing composition of the invention, to the closed sutured internal hole. In certain embodiments, e.g., wherein the first delivery of cells is insufficient, the method may further comprise: (c) delivering a second dose of at least about $20\times10^6$ cells, at least about $30\times10^6$, or at least about $40\times10^6$ adipose tissue-derived stromal stem cells, e.g., in an adipose tissue-derived stromal stem cell-containing composition of the invention, to the closed sutured internal hole.

In another embodiment, the adipose tissue-derived stromal stem cell-containing composition used in the method is one wherein at least about 50%, at least about 60%, at least about 70%, at least about 80%, at least about 85%, at least about 90%, at least about 95% or preferably at least about 96%, 97%, 98% or 99% of the stem cells express the CD9, CD10, CD13, CD29, CD44, CD49A, CD51, CD54, CD55, CD58, CD59, CD90 and/or CD105 markers.

In another embodiment, the adipose tissue-derived stromal stem cell-containing composition used in the method is one wherein at least about 50%, at least about 60%, at least about 70%, at least about 80%, at least about 85%, at least about 90%, at least about 95% or preferably at least about 96%, 97%, 98% or 99% of the stem cells express the c-Kit, vimentin and/or CD90 markers.

Common methods of administering the cells of the present invention to subjects, particularly human subjects, some of which are described in detail herein, include injection or implantation of the cells into target sites in the subjects, the cells of the invention can be inserted into a delivery device which facilitates introduction by, injection or implantation, of the cells into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The cells of the invention can be inserted into such a delivery device, e.g., a syringe, in different forms. For example, the cells can be suspended in a solution or embedded in a support matrix when contained in such a delivery device. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating progenitor cells as described herein in a pharmaceutically acceptable carrier or diluent and, as required, other ingredients enumerated above, followed by filtered sterilization.

In other embodiments, a method of treating a fistula in a subject comprises: (a) closing the internal hole with a suture that comprises adipose tissue-derived stromal stem cells, e.g., from a subject adipose tissue-derived stromal stem cell-containing composition. Such sutures coated with cells in the subject adipose tissue-derived stromal stem cell-containing compositions are described in detail, in U.S. patent application Ser. No. 11/056,241, filed on Feb. 14, 2005, which is incorporated herein by reference.

The methods may in some embodiments further comprise: (d) deep scraping of at least one fistula track and (e) filling said fistula track with a material. In certain embodiments, the method may further comprise delivering at least about $10\times10^6$ adipose tissue-derived stromal stem cells, e.g., from a subject cellular composition, to the material. Preferably, the material is a fibrin-based polymer or adhesive, such as a fibrin glue or gel. In certain embodiments, the dose of at least about $10\times10^6$ adipose tissue-derived stromal stem cells is already encompassed within the material, e.g., such that the material comprises the adipose tissue-derived stem cell containing-composition.

The methods of the invention may be used to treat any fistula, including but not limited to anorectal fistula or fistula-in-ano or fecal fistula, arteriovenous fistula or A-V fistula, biliary fistula, cervical fistula, craniosinus fistula, enteroenteral fistula, enterocutaneous fistula, enterovaginal fistula, gastric fistula, metroperitoneal fistula perilymph, pulmonary arteriovenous fistula, rectovaginal fistula, umbilical fistula, tracheoesophageal fistula and vesicovaginal fistula. Preferably, the methods may be used to treat intestinal fistulae, e.g. those connecting the intestine to itself or to another organ, such as rectovaginal fistula, enteroenteral fistula, enterocutaneous fistula and enterovaginal fistula. In another preferred embodiment, the methods may be used to treat vaginal or uterine fistulae, e.g. those connecting the vagina or uterus to itself or to another organ, such as cervical fistula, rectovaginal fistula, enterovaginal fistula, and vesicovaginal fistula.

The fistula may be accessed for surgical repair via any method known in the art, e.g., via incision, catheter, etc.

In another embodiment, a method of treating a wound in a subject comprises: (a) closing the wound with a suture and (b) delivering at least about $10 \times 10^6$, at least about $20 \times 10^6$, at least about $30 \times 10^6$, or at least about $40 \times 10^6$ adipose tissue-derived stromal stem cells, e.g., in an adipose-tissue derived stromal stem cell-containing composition, to the closed sutured wound. In certain embodiments, e.g., wherein the first delivery of cells is insufficient, the method may further comprise: (c) delivering a second dose of at least about $20 \times 10^6$ cells, at least about $30 \times 10^6$, or at least about $40 \times 10^6$ adipose tissue-derived stromal stem cells, e.g., in an adipose-tissue derived stromal stem cell-containing composition, to the closed sutured wound. In other embodiments, the wound may be filled with an adipose-tissue derived stromal stem cell-containing composition of the invention, e.g. a dose of at least about $10 \times 10^6$ adipose tissue-derived stromal stem cells encompassed within a material, e.g., such that the material comprises the cellular composition, wherein the material is, for example, an adhesive or glue. In other embodiments, a method of treating a wound in a subject comprises: (a) closing the wound with a suture that comprises adipose tissue-derived stromal stem cells, e.g., from a subject adipose-tissue derived stromal stem cell-containing composition. Such sutures coated with cells from the subject adipose tissue-derived stromal stem cell-containing compositions are described in detail above and in U.S. patent application Ser. No. 11/056,241, filed on Feb. 14, 2005, which is incorporated herein by reference.

The methods described above may further comprise administering a therapeutic agent to the subject being treated, e.g. systemically or locally at the site of suturing. In certain embodiments, the adipose tissue-derived stromal stem cells are formulated in an adipose tissue-derived stromal stem cell-containing composition which contains a therapeutic agent, as described above. In other embodiments, the therapeutic agent is administered separately, e.g. simultaneously with the methods, before the method is performed, or after the method is performed. In some embodiments, the therapeutic agent is administered to the subject before, during and after the methods are performed on the subject. Exemplary therapeutic agents are described above. In preferred embodiments, therapeutic agents for the treatment of Crohn's disease are administered to the subject. Exemplary Crohn's disease therapeutic agents are antiinflammatory agents such as agents comprising mesalamine, immunosuppressive agents such as 6-mercaptopurine and azathioprine; biological agents such as infliximab (REMICADE®), antibiotics, and antidiarrheal agents such as diphenoxylate, loperamide, and codeine.

In embodiments wherein allogeneic stem cells are used, supportive treatment may be required. For example, immunosuppressants may be administered before, during and/or after treatment to prevent GVHD, according to methods known in the art. Prior to administration, the cells may also be modified to suppress an immune reaction from the subject to the cells or vice-versa, according to methods known in the art.

The dosage of any therapeutic agent will vary depending on the symptoms, age and body weight of the patient, the nature and severity of the disorder to be treated or prevented, the route of administration, and the form of the agent. Any of the subject formulations may be administered in a single dose or in divided doses. Dosages for the therapeutic agents may be readily determined by techniques known to those of skill in the art or as taught herein. Also, mixtures of more than one therapeutic agent may be administered, or multiple therapeutic agents administered in separate compositions.

Therapeutic agents can be administered orally, parenterally, by inhalation spray, topically, rectally, nasally, buccally, vaginally, or via an implanted reservoir. The term parenteral as used herein includes subcutaneous, intracutaneous, intravenous, intramuscular, intra articular, intrasynovial, intrasternal, intrathecal, intralesional, and intracranial injection or infusion techniques.

The precise time of administration and amount of any particular agent that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several therapeutic agents may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the agents to the desired site in order to reduce side effects.

The data obtained from the cell culture assays and animal studies may be used in formulating a range of dosage for use in humans. The dosage of any therapeutic agent or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

5. Kits

In other embodiments, the invention contemplates kits including the adipose tissue-derived stromal stem cell-containing compositions and optionally instructions for their use. Kits comprising the pharmaceutical compositions and biomaterials of the present invention are also within the scope of the invention. Kit components may be packaged for either manual or partially or wholly automated practice of the foregoing methods. Such kits may have a variety of uses, including, for example, therapy, repair, preparation of biomaterials and other applications.

EXEMPLIFICATION

The invention now being generally described, it will be more readily understood by reference to the following examples, which are included merely for purposes of illustration of certain aspects and embodiments of the present invention, and are not intended to limit the invention.

Example 1

Preparation of Stem Cells from Lipoaspirates with Improved Homogeneity

Adipose tissue was obtained by liposuction, under local anaesthesia and general sedation. A hollow blunt-tipped cannula was introduced into the subcutaneous space through a small incision (less than 0.5 cm in diameter). With gentle suction, the cannula was moved through the adipose tissue abdominal-wall compartment for mechanical disruption of the fatty tissue. A saline solution and the vasoconstrictor epinephrine were injected into the adipose tissue compartment to minimize blood loss. In this way, 80 to 100 ml of raw of lipoaspirate were obtained from each patient to be treated.

The raw lipoaspirate was washed extensively with sterile phosphate-buffered saline (PBS; Gibco BRL, Paisley, Scotland, UK) to remove blood cells, saline and local anaesthetic. The extracellular matrix was digested with a solution of type II collagenase (0.075%; Gibco BRL) in balanced salt solution (5 mg/ml; Sigma, St. Louis, USA) for 30 min at 37° C. to release the cellular fraction. Then the collagenase was inactivated by addition of an equal volume of Dulbecco's modified Eagle's medium (DMEM; Gibco BRL) that contained 10% fetal bovine serum (FBS; Gibco BRL). The suspension of cells was centrifuged at 250×g for 10 min. Cells were resuspended in 0.16 M $NH_4Cl$ and allowed to stand for 10 min at room temperature (RT) for lysis of erythrocytes. The mixture was centrifuged at 250×g, and cells were resuspended in DMEM plus 10% FBS and 1% ampicillin/streptomycin mixture (Gibco, BRL) and then they were plated in 100-mm tissue culture dishes at a concentration of $10-30×10^3$ cells/$cm^2$.

Cells were cultured for 24 h at 37° C. in an atmosphere of 5% $CO_2$ in air. Then the dishes were washed with PBS to remove non-adhering cells and cell fragments. The cells were maintained in culture in the same medium and under the same conditions until they reached approximately 80% confluence, with replacement of the culture medium every 3 to 4 days. Cells were then passaged with trypsin-EDTA (Gibco BRL) at a dilution of 1:3 which corresponds to a cell density of approximately about $5-6×10^3$ cells/$cm^2$. For transplantation, we used cells between passages 1 and 3, with cells having been passaged more than twice being preferable in order to isolate a cell population with high homogeneity. Cell characterization was performed using cells at passages 1 to 9.

Example 2

Characterization of Stem Cells from Lipoaspirates with Improved Homogeneity

To characterize the cells by immunofluorescence staining, cells were plated at low density in DMEM plus 10%) FBS on glass cover slips in 24-well plates. For immunohistochemistry studies, cells were washed with PBS and fixed in acetone for 10 min at −20° C. For staining of a-actin, cells were fixed in 4% paraformaldehyde for 10 min at RT. After blocking with a PBS that contained 4% goat serum and 0.1% Triton X-100, cells were incubated at 4° C. overnight with primary antibodies against the following cell markers at the indicated dilutions [(i) alpha-actin; Dako, Glostrup, Denmark; 1/50; (ii) vimentin; Sigma, St. Louis, USA; 1/200; (iii) CD 90; CYMBUS, Biotechnology LTD, Chandlers Ford, Hants, UK; 1/50; (iv) Factor VIII; Dako; 1/100; (v) CD 34; Chemicon, CA, USA; 1/100; (vi) c-Kit; Chemicon; 1/100; (vii) desmin; Dako; 1/100; (viii) cytokeratin; Dako; 1/100 and (ix) S-100; Dako; 1/50]. Then cells were incubated with the appropriate Fluorescein isothiocyanate (FITC)-conjugated or Tetramethylrhodamine isothiocyanate chloride (TRITC)-conjugated second antibodies (Sigma; 1/50) for 45 min at RT. For negative controls we omitted the primary antibodies. Nuclei were counterstained with 4',6-diamidino-2-phenylindole (DAPI). Cells were then mounted in Mobiglow (MoBiTec, Gottingen, Germany) and observed with an epifluorescence microscope Eclipse TE300 (Nikon, Tokyo, Japan). In each case, we determined the numbers of immunopositive cells in different fields and compared them to the numbers of stained nuclei. Randomly selected fields were exported to a computer (Macintosh G3; Apple Computer Inc., Cupertino, Calif., USA) through a Spot1 camera (Diagnostic Instruments Inc., Tampa, Fla., USA). Human aortic smooth muscle cells, human umbilical vein endothelial cells (HUVEC) and human synovial fibroblasts were used as positive controls for immunostaining with the various antibodies.

At passage 1, a high percentage (90-95%) of adipose-derived stromal stem cells expressed vimentin, a marker of mesenchymal cytoskeletal cells (FIG. 1). Expression of vimentin was maintained at the same level up to and including passage 9. Levels of other markers fell, however, with time. For example, a-actin, which was found in 17% of LPA-derived cells at passage 1 was no longer detectable at passage 7. The marker of endothelial cells, von Willebrandt factor (Factor VIII), and CD34, which is also found on the surface of endothelial cells, were only detected at passages 1 through 3 (7% and 12%) immunopositive cells, respectively). By contrast, the expression of c-Kit (CD 117), a marker of cell proliferation, increased with time, with 99% immunopositive cells from passage 4 onwards (FIG. 2). The fibroblast marker CD90, initially expressed in approximately 80% of LPA-derived cells, was found in 99% of cells from passage 6 (FIG. 3). No expression of the neuroectodermal marker S100 or the ectodermal marker keratin was observed in any of the LPA-derived cells at any time. The change in observed markers as the number of passages increases indicates an increase in the homogeneity of the cell preparation obtained.

To quantitate cell growth, cells were plated in 24-well plates at a concentration of $5 \times 10^3$ cells/cm$^2$. After cells had attached to the substratum (3 h), the culture medium was replaced by DMEM supplemented with 1% antibiotics plus 0.5%, 2%, 5% or 10% FBS. As positive controls for testing of each batch of serum, human synovial fibroblasts were also cultured and their growth rates determined. Medium was replaced every two days. At 24-h intervals, cells were fixed with 1% glutaraldehyde and the number of cells per well was determined, after nuclear staining with crystal violet, by monitoring absorbance at 595 nm. A standard curve was constructed to establish the relationship between cell number per well and absorbance at 595 nm ($r^2=0.99$).

Figure 4:
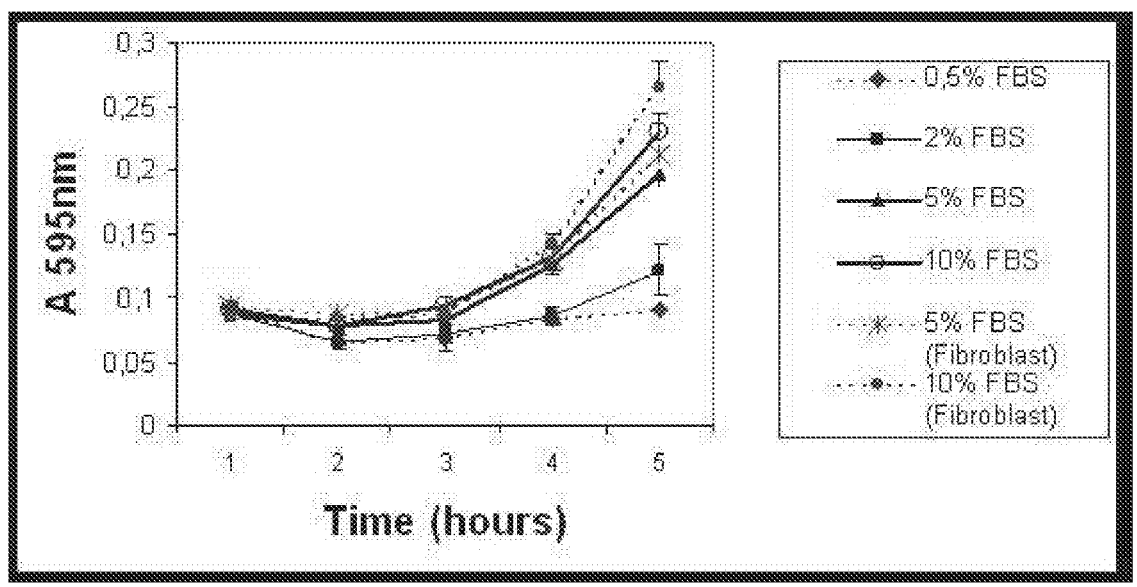
FIG. 4 depicts growth curves of lipoaspirate-derived cells at different concentrations of FBS (0.5, 2.5 and 10%, as indicated). Human synovial fibroblasts were cultured in the presence of either 5% or 10% FBS. Cell numbers±SD are shown in terms of absorbance at 595 nm. Data are from a representative experiment with triplicate wells.

Viable adipose tissue-derived stromal cells were successfully isolated and cultured from all seven lipoaspirates (LPAs). These cells were grown in culture and passaged at 7 to 10 day intervals. In some cases, cells were cryopreserved and thawed prior to implantation. The growth rate of adipose tissue-derived stromal stem cells (ADSC) depended on the serum concentration, with maximal proliferation between 5% and 10% FBS (FIG. 4). The mean population-doubling time at these concentrations of serum was 37.6±0.6 h, which did not differ significantly from the population-doubling time of human synovial fibroblasts cultured under the same conditions (35.6±1.4 h; p>0.05; t-test; results from three independent experiments).

In order to analyze the cells in a more standardized and less subjective manner, the cells were also subjected to Fluorescence Activated Cell Sorter (FACS) analysis. In general, the flow cytometry analysis permits the detection of surface antigens by antibodies, which are directly (covalently) or indirectly (secondary fluorescent-labeled antibody) linked to a fluorescent marker. On the other hand, the above described immunohistochemical analysis demanded permeabilization of the cells and the subsequent staining with antibodies. Thus, the latter requires an individually optimized protocol depending on target protein and antibody. Moreover, due to the permeabilization of the cell membrane, it is not possible to distinguish between internal (non-membrane bound) and extracellular marker proteins. That is, with an immunohistochemical analysis it is possible to know if a protein marker is being expressed but it is not possible to distinguish if it is being expressed at the cell surface or intracellularly.

The protocol used in the immunocytometry for the detection of surface antigens is standardized, and only requires appropriate negative controls. Further, the FACS analysis allows an evaluation of the percentage of positive cells (cells expressing the surface antigen), and the level of expression (few or many surface antigens on one cell). These evaluations are only of subjective nature using immunohistochemistry, and may vary from experiment to experiment, which does not occur with the FACS analysis.

Such immunophenotypic characterization of the cells may be performed on freshly isolated cells and after periods of cultures, for example, at day 7, after 4 weeks and after 3 months of culture. The analysis of surface markers at different times allows the assessment of the homogeneity of the phenotype during culturing. Examples of this analysis and data demonstrating the phenotype obtained from samples obtained from 3 healthy donors from zero to three months of culturing are described at length in U.S. patent application Ser. No. 11/065,461, filed on Feb. 25, 2005, which is incorporated herein by reference.

After isolation by the above described method, the adipose-derived stromal stem cells from one of the patients were characterized in function of the presence/absence of a series of surface markers. To do this, the expression of the following surface markers was monitored by flow cytometry:

Integrin: CD11b, CD18, CD29, CD49a, CD49b, CD49d, CD49e, CD49f, CD51, CD61, CD104.

Hematopoietic markers: CD3, CD9, CD10, CD13, CD16, CD14, CD19, CD28, CD34, CD38, CD45, CD90, CD133, glicoforine.

Growth factor receptors: CD 105, NGFR.

Extracellular matrix receptors: CD15, CD31, CD44, CD50, CD54, CD62E, CD62L, CD62P, CD102, CD106, CD146, CD166.

Others: CD36, CD55, CD56, CD58, CD59, CD95, HLA-I, HLA-11, B2-microglobuline.

The cells to be characterized were collected by means of gentle digestion with trypsin, washed with PBS and incubated for 30 minutes at 4° C. with fluorescein (FITC) or phycoerythrin (PE) labeled antibody markers against each one of the surface markers to be analyzed. The cell markers were washed and immediately analyzed using the Epics-XL cytometer (Coulter). As controls, cells stained with unspecific antibodies of the corresponding isotopes labeled with FITC or PE were used.

Figure 7A:
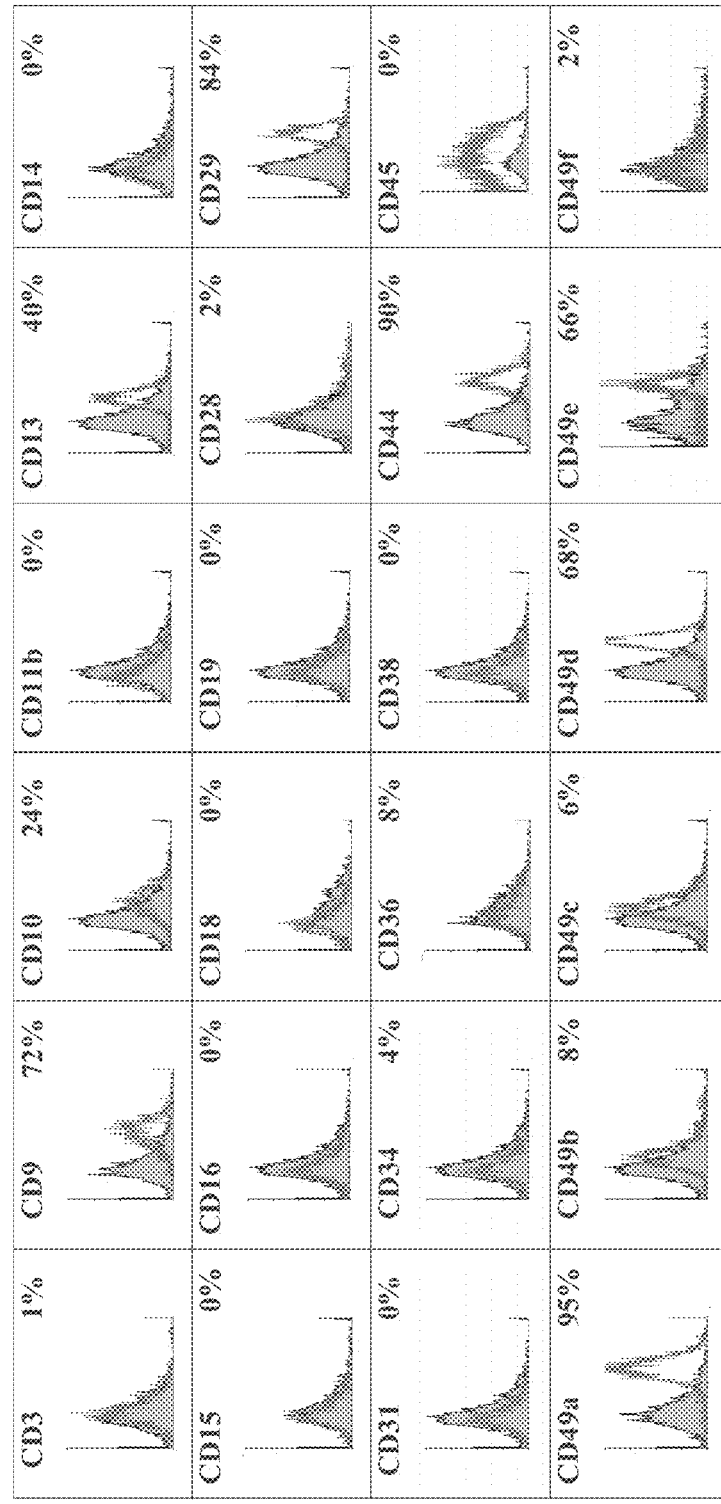
FIG. 7A depicts histograms of fluorescence immunocytometry corresponding to the profile of surface markers (CD3, CD9, CD10, CD11b, CD13, CD14, CD15, CD16, CD18, CD19, CD28, CD29, CD31, CD34, CD36, CD38, CD44, CD45, CD49a, CD49b, CD49c, CD49d, CD49e and CD49f) obtained from cells isolated from liposuction samples of a patient involved in the study, at passage 6. For each histogram, the x-axis extends on a logarithmic scale from $10^0$ (left side of graph) to $10^4$ (right side of graph), and the y-axis extends on a linear scale from 0 (bottom of graph) to 16 (top of graph) (except for CD45, which extends to 64).
Figure 7B:
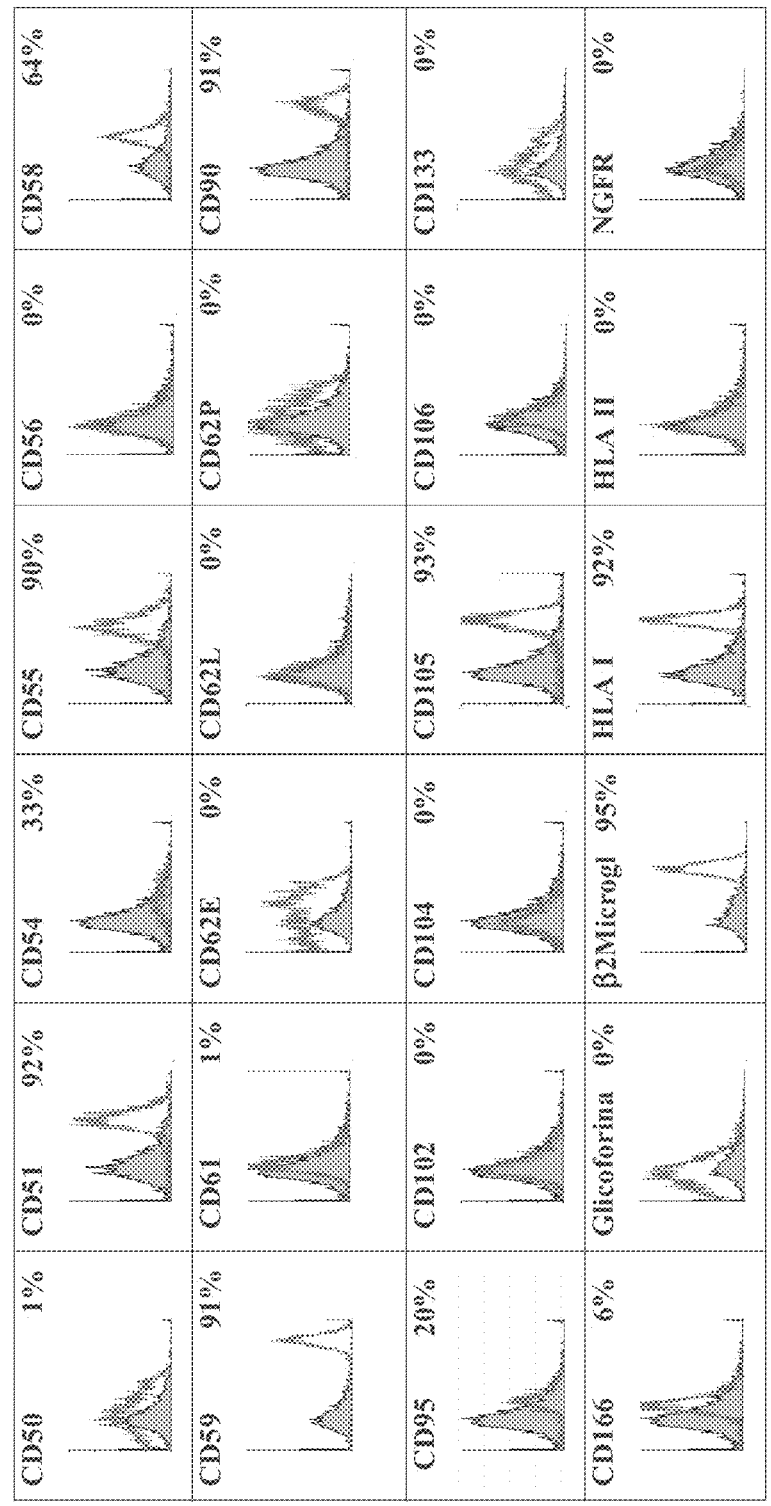
FIG. 7B depicts histograms of fluorescence immunocytometry corresponding to the profile of surface markers (CD50, CD51, CD54, CD55, CD56, CD58, CD59, CD61, CD62E, CD62L, CD62P, CD90, CD95, CD102, CD104, CD105, CD106, CD133, CD166, glicoforina, ß2 microglobuline, HLA I, HLA II and NGFR) obtained from cells isolated from liposuction samples of a patient involved in the study, at passage 6. For each histogram, the x-axis extends on a logarithmic scale from $10^0$ (left side of graph) to $10^4$ (right side of graph), and the y-axis extends on a linear scale from 0 (bottom of graph) to 16 (top of graph) (except for CD50, CD58, CD59, CD62E, CD133, glicoforina, and ß2 microglobuline, which each extend to 32).

From the analysis of the profile of expression of surface markers (FIG. 7A/7B), the criteria used to determine which markers define the cell population and allow it to be identified and differentiated with respect to other types of cell were the following:

1. Discard those markers that vary from one sample to the other or over time during culturing in the experimentation done with healthy donors' adipose-derived stromal stem cells in the U.S. patent application Ser. No. 11/065,461, filed on Feb. 25, 2005, which is incorporated herein by reference.

2. Select the markers as a function of their biological relevance, discarding markers characteristic of specific cell types (for example, CD3 is a marker exclusive to lymphocytes).

Applying these criteria, the multipotent stem cell population is characterized as being positive for CD9+, CD10+, CD13+, CD29+, CD44+, CD49A+, CD51+, CD54+, CD55+, CD58+, CD59+, CD90+ and CD105+: and lacking expression of CD11b, CD14, CD15, CD16, CD31, CD34, CD45, CD49f, CD102, CD104, CD106 and CD133.

Example 3

Preparations of Stem Cells Comprising Fibrin Glue for Use in Treating Fistula

For clinical use, the cells as prepared above may be used after three or fewer passages (FIG. 3), but are preferably used after two or more passages as described above to afford a cell preparation with higher homogeneity. Cell cultures for clinical use were trypsinized for 3 min at 37° C. Trypsinization was stopped by addition of DMEM plus FBS, and the suspension was centrifuged at 110×g for 5 min. Cells were washed in PBS and the suspension was centrifuged again at 150×g for 5 min. Cell were resuspended at between 3 and 30×10$^6$ cells/ml in 1 to 2 ml of Ringer's lactate solution and put in a suitable syringe. Human serum albumin (HSA) may optionally be added to the Ringer's lactate solution.

In certain cases, half of the cells were resuspended in the thrombin component of a fibrin glue kit (TISSUCOL® Duo 2.0; Baxter, Madrid, Spain) prior to combination of the kit's two components, in an attempt to improve the obturation of the fistulae' tracts. The use of fibrin glue to fill a fistula opening is known in the art; however, it is not efficient as a standalone treatment for fistula. The addition of fibrin glue to the adipose tissue-derived stromal stem cell-containing compositions described herein serves to retain cells locally, and we have observed that the cells grow well inside fibrin glues and gels.

Example 4

Improved Surgical Procedure to Repair Fistula Using Preparations of Stem Cells from Lipoaspirates We conducted a phase I clinical trial designed to test the feasibility and safety of autologous stem cell transplantation using the above-described adipose tissue stromal stem-cell compositions for treatment of Crohn fistulae. The protocol was approved by the Clinical Trial and Ethics Committee of La Paz Hospital on Apr. 12, 2002, and a detailed informed-consent form was generated to be signed by patients. The Ethics Committee was kept informed about the progress of the study throughout the clinical trial Methods The patients were selected according to the following inclusion criteria: more than 18 years of age; diagnosis of Crohn's disease at least five years prior to the trial; presence of one or more complex Crohn fistulae (enterocutaneous fistula, suprasphincteric fistula and/or rectovaginal fistula) that had been unresponsive to medical treatment and unsuccessfully treated by classical surgery at least twice; and agreement to participate, with signature of the informed-consent form. The exclusion criteria were as follows: Failure to meet inclusion criteria; mental handicap; extreme thinness; allergy to local anaesthetics; prior diagnosis of cancer; and AIDS.

Five patients (nos. 001-005) were enrolled in the study. There were three men and two women, and the average age was 35.1±2.4 years (range: 31.2 to 37.5 years). Nine cell implants were performed: three in recto-vaginal fistulae; five in enterocutaneous fistulae (four different fistulae in one patient; and one in a suprasphincteric perianal fistula. All enterocutaneous fistulae had low flow—less than 50 cc per day- and were located in the abdominal wall (Table 1). No patient was treated with Total Parenteral Nutrition, Remicaid or Octreotride concurrently with this procedure. Patients 001 and 002 required two liposuction procedures because, after the first liposuction, no stem cells survived cryopreservation.

One patient was excluded due to bacterial contamination of cultured cells. We inoculated nine fistulae in four patients with autologous adipose tissue-derived stromal stem cells (ADSC) at passage three or earlier. Eight inoculated fistulae were followed weekly for at least eight weeks. In six fistulae, the external opening was covered with epithelium at the end of week 8 and, thus, these fistulae were considered healed (75%). In the other two fistulae, there was only incomplete closure of the external opening, with a decrease in output flow (not healed; 25%). No adverse effects were observed in any patient at the end of the follow-up period (at least six months and no more than two years).

In the case of enterocutaneous fistulae, all tracks were deep scraped. In the case of recto-vaginal fistulae, we used a vaginal approach, with detachment of the posterior vaginal wall. The gap was completely separated and the rectal opening was closed with 3/0 absorbable stitches. The rectal mucosa had been damaged by Crohn's disease and was extremely fragile. In the case of perianal fistulae, the main track was cored out and the rectal hole was closed with 3/0 absorbable stitches through the sclerotic mucosa.

Figure 5:
FIG. 5 depicts the blister in the rectal mucosa after cells had been injected close to the sutured internal opening.

Using a needle, in cases of enterocutaneous fistula, we injected cells into the wall of the track. In the cases of recto-vaginal and perianal fistulae, we injected cells into the rectal mucosa, close to the sutured internal opening. In all cases, we observed a fluid-filled blister on the area of the injection after the injection (FIG. 5). The number of injected cells ranged from 3 to 30×10$^6$, depending on the growth of the cultured cells (FIG. 3).

The time from the beginning of preparation of the inoculum to the end of the injection v/as less than 90 minutes in all cases. In the case of enterocutaneous fistulae, tracks were filled with fibrin glue and then the skin was sutured. In case of recto-vaginal fistulae, an advancement vaginal flap was constructed. When accessory tracks were detected, they were also filled with fibrin glue. No bandages were applied post-operatively. Liquid intake was initiated twelve hours after the procedure and solid food six hours afterwards. One to three days after surgery, the patient was dismissed and follow-up visits were scheduled at the out-patient clinic.

Two histopathological samples were obtained. One specimen (patient number 002) was obtained from the area of an enterocutaneous fistula (7 months after implant #2 and 10 days after implant #3). The other specimen (patient number 001) was obtained from the recto-vaginal wall, one year after the first implant, (implant #1), during the surgical procedure associated with implant #6. The specimens were embedded in paraffin, sectioned, stained with haematoxylin and eosin, and evaluated.

Weekly follow-up was scheduled for eight weeks after surgery. Patients were considered healed when a total epithelialization of the external opening was evident after eight weeks, independently of prior observations. After eight weeks, there was a monthly follow-up for at least six months and not more than two years.

Results

Five patients were included in the study and seven liposuctions were performed (FIG. 3). Patient number 003 was eliminated from the trial during the implant procedure as a result of the discovery of contamination by Gram-positive bacteria of the cultured lipoaspirated cells. The bacteria were identified as *Oerkovia xanthineolytica*. An enterocutaneous fistula in patient 002 was eliminated from the study because of emergency abdominal surgery for a new enterovesicular fistula that had resulted in acute sepsis. The laparotomy required the resection of the implant area. Therefore, we could not adhere to the minimum eight-week follow-up schedule in this case.

Figure 6:
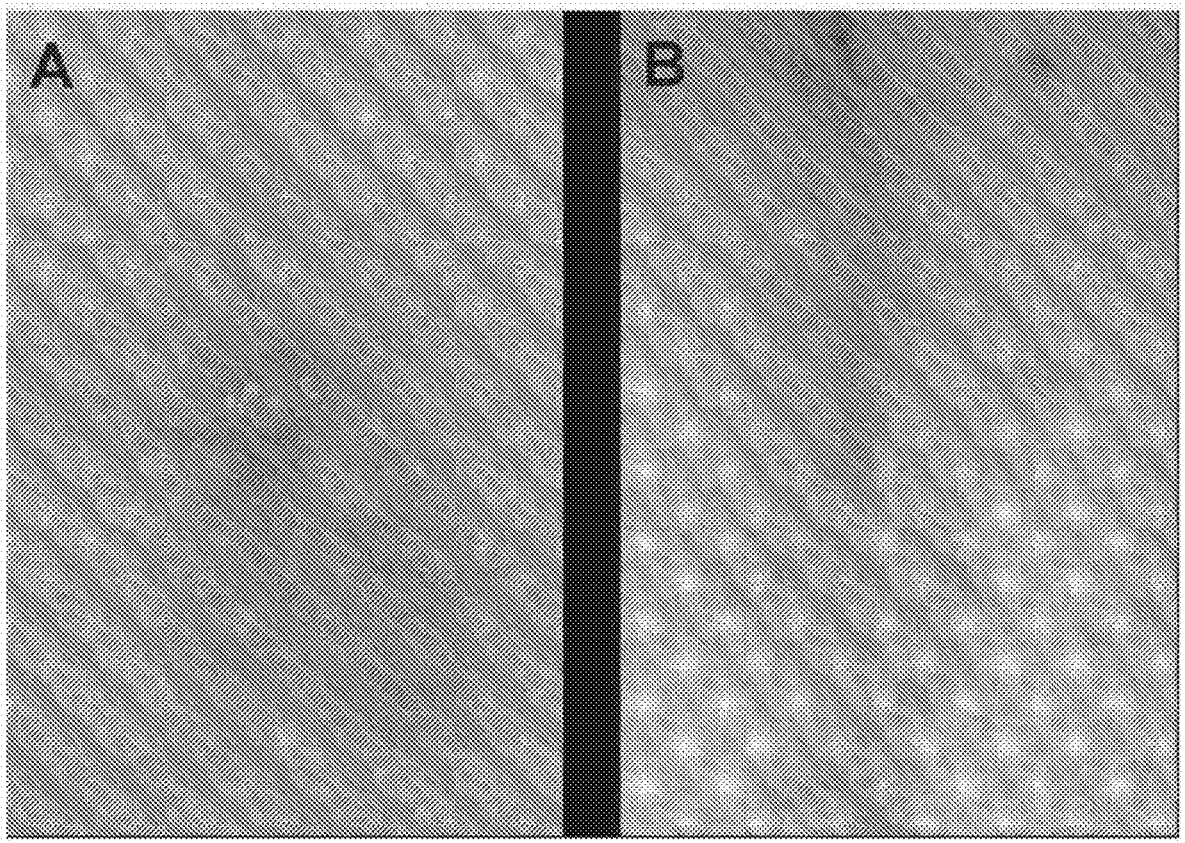
FIG. 6 depicts photographs of a fistula before (A) and eight weeks after (B) injection of cells.

Nine fistulae from four patients were inoculated with ADSC after three or fewer passages (FIG. 3). Eight fistulae were considered suitable for retention in the study and followed for at least eight weeks (FIG. 3). In six fistulae, the external opening had epithelialized by week 8 and these fistulae were considered healed (75%) (FIG. 6). The other two had only incomplete closure of the external opening, with a decrease in output flow, as reported by the patients (25%; not healed; FIG. 3). There was no direct relationship between the number of cells injected or culture time and success of the procedure. There was also no direct relationship between the patient's gender or age and healing. Subsequence studies we have done indicate that an initial dose of $20 \times 10^6$ cells is suitable. We have determined that a second dose of $40 \times 10^6$ cells may be used in the event that the first dose fails. Higher cell doses are preferred because we have observed that higher cell numbers have a better therapeutic effect in tissue repair.

Surgical and implantation procedures were performed without additional technical difficulty in all nine treated fistulae. No immediate adverse reactions (e.g., anaphylaxis, allergic reactions) were observed in any of the cases studied.

Two histopathological samples were obtained seven months (enterocutaneous fistula) and one year (recto-vaginal fistula) after surgery. No cytological transformation was detected in a complete series of histopathological sections.

Discussion

In a previous report, we described the successful cell-based treatment of a young woman with a recurrent recto-vaginal fistula that had been unresponsive to medical treatment. Thus, we designed the present phase I clinical trial to evaluate the feasibility and safety of such autologous adipose tissue stromal stem-cell transplantation (with improvements in the original protocol) for the treatment of unresponsive Crohn fistulae, as well as to test the use of adipose tissue stromal stem-cells in conjunction with a fibrin glue.

We chose adipose tissue as the source of stem cells because of their capacity for myogenic differentiation and the fact that fistulae respond well to muscle transplants. Moreover, liposuction fat is available in large quantities and can be harvested with minimal adverse effects on the patient. Other groups have used bone marrow-derived stem cells but, in such cases, a cell-mobilization procedure is required that can be dangerous to some patients, such as those with a myocardial infarction. In our study, all liposuction procedures yielded a clinically useful number of cells with characteristics of stem cells.

We followed our patients according to the program scheduled, and we observed a complete healing in 6 of 8 procedures. It is important to note that Crohn's disease provides the worst conditions for a surgical approach to fistulae because of the fragility of the tissue and the enormous problems associated with healing in these patients. Our patients were chosen because they had been unresponsive to medical treatment and at least two previous surgical procedures but our treatment seemed to be quite effective. Nevertheless, new outbreaks of Crohn's disease may still produce new fistulae in any given patient that will need to be treated again using the cryopreserved autologous cells from that patient.

The biological mechanism that underlies the therapeutic success of ADSC transplantation is unknown. Stem cells might differentiate into connective, muscle or scar tissue. Alternatively, secretion of growth factors by the stem cells might facilitate wound healing. We saw typical scar tissue in the histopathologically examined fistulae, but we have no way of distinguishing transplanted from local connective-tissue cells. We observed a complete healing in 75% of cases using our treatment.

REFERENCES

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

1. American Gastroenterological Association Medical Position Statement: Perianal Crohn's Disease. *Gastroenterology* (2003) 125:1503-1507.
2. Levy C, Tremaine W J. *Inflamm Bowel Dis* (2002) 8(2):106-11.
3. Pennincke F, D'Hoore A, Filez L. *Acta Gastroenterol Belg* (2001) 64(2):223-226.
4. Rius J, Nessim A, Nogueras J J, Wexner S D. *Eur J Surg* (2000) 166(3):218-222.
5. Mizuno H, Zuk P A, Zhu M, Lorenz H P, Benhaim P, Hedrick M H. *Plastic Reconstr Surg* (2002) 109(1): 199-209.
6. Zuk P A, Zhu M, Mizuno H, et al. *Tissue Eng* (2001) 7(2): 211-228.
7. Garcia-Olmo D, Garcia-Arranz M, Gomez-Garcia L et al. *Int J Colorectal Dis* (2003) 18:451-454.
8. Abkowitz J L. *New Engl J Med* (2002) 346(10): 770-772.
9. Matsubara H. *Lancet* (2004) 363:746-747.
10. Cowan C M, Shi Y Y, Aalami 00, et al. *Nat Biotechnol.* (2004) 22(5):560-7
11. Garcia-Olmo D, Garcia-Olmo M A. *New Eng J Med* (2003) 349: 1480-1481.
12. Osawa M., Hanada K., Hanada H. and Nakauchi H. (1996) *Science* 273, 242-245.
13. Morrison S. J., Uchida N. and Weissman I. L. (1995) *Annu. Rev. Cell Dev. Biol.* 11, 35-71.
14. Ivanova N. B., Dimos J. T., Schaniel C., Hackney J. A., Moore K. A., Lemischka* I. R. (2002) *Science* 298, 601-604.
15. Phillips R L. (2000) *Curr Top Microbiol Immunol.* 251, 13-19.
16. Ramalho-Santos M, Yoon S, Matsuzaki Y, Mulligan R C, Melton D A. (2002) *Science* 298, 597-600.
17. De Ugarte D A, Morizono K, Elbarbary, AAlfonso Z, Zuk P A, Zhu M, Dragoo J L, Ashjian P, Thomas B, Benhaim P, Chen I, Fraser J, Hedrick M H. (2003) *Cells Tissues Organs* 174 (3), 101-109.

18. Friedenstein A J, Gorskaja J F, Kulagina N N, *Exp Hematol*. (1976) September; 4(5):267-74.
19. Caplan A I *J Orthop Res*. (1991) September; 9(5):641-50
20. Pittenger, M. F. et al. (1999) *Science* 284: 143-147
21. Beresford J N, Bennett J H, Devlin C, Leboy P S, Owen M E, *J Cell Sci*. (1992) June; 102 (Pt 2):341-51
22. Yoo J U, Johnstone B, *Clin Orthop*. (1998) October; (355 Suppl):S73-81
23. Wakitani S. et al. (1995) *Muscle Nerve* 18: 1417-1426.
24. Haynesworth S E, Goshima J, Goldberg V M, Caplan A I, *Bone*. 1992; 13(1):81-8.
25. Sanchez-Ramos J, Song S, Cardozo-Pelaez F, Hazzi C, Stedeford T, Willing A, Freeman T B, Saporta S, Janssen W, Patel N, Cooper D R, Sanberg P R, *Exp Neurol*. (2000) August; 164(2):247-56.
26. Rogers J J, Young H E, Adkison L R, Lucas P A, Black A C Jr, *Am Surg*. (1995) March; 61(3):231-6.
27. Jiang Y, Vaessen B, Lenvik T, Blackstad M, Reyes M, Verfaillie C M, *Exp Hematol*. (2002) August; 30(8):896-904.
28. Caplan A I, Bruder S P, *Trends Mol Med*. (2001) June; 7(6):259-64.
29. Stanford, C. M. et al. (1995) *J Biol Chem* 270: 9420-9428.

EQUIVALENTS

The present invention provides, among other things, methods and compositions for treating and preventing fistula. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

We claim:

1. A method of preparing a pharmaceutical composition, comprising thawing a cryopreserved composition and formulating the thawed composition with human serum albumin (HSA) and Dulbecco's Modified Eagle's Medium (DMEM) to produce the pharmaceutical composition, wherein the cryopreserved composition comprises an isolated cell population comprising adipose tissue-derived stromal stem cells, wherein the isolated cell population was ex vivo generated by passaging adherent cells obtained from adipose tissue at least four times so that fewer than 10% of the adipose tissue derived stromal cells in the cryopreserved composition express the CD34 marker as measured by flow cytometry and at least 50% of the adipose-tissue derived stromal cells in the cryopreserved composition express the CD90 marker as measured by flow cytometry, wherein the concentration of the adipose tissue-derived stromal stem cells in the cryopreserved composition is at least about $5\times10^6$ cells/mL.

2. The method of claim 1 wherein at least 85% of the adipose tissue-derived stromal stem cells in the cryopreserved composition express the CD44 marker and more than 50% of the adipose tissue-derived stromal stem cells express the CD29 and CD105 markers as measured by flow cytometry.

3. The method of claim 1 wherein at least 95% of the adipose tissue-derived stromal stem cells in the cryopreserved composition express the CD44 marker as measured by flow cytometry.

4. The method of claim 1 wherein at least 99% of the adipose tissue-derived stromal stem cells in the cryopreserved composition express the CD44 marker as measured by flow cytometry.

5. The method of claim 1 wherein the adherent cells obtained from adipose tissue were passaged at least six times.

6. The method of claim 1, wherein the cryopreserved composition further comprises HSA.

7. A method of preparing a pharmaceutical composition, comprising formulating an isolated cell population with HSA and DMEM to produce the pharmaceutical composition, wherein the isolated cell population comprises adipose tissue-derived stromal stem cells, wherein the isolated cell population was ex vivo generated by and passaging adherent cells from adipose tissue at least four times so that fewer than 10% of the adipose tissue-derived stromal stem cells in the pharmaceutical composition express the CD34 marker as measured by flow cytometry and at least 50% of the adipose tissue derived stromal stem cells in the pharmaceutical composition express the CD90 marker as measured by flow cytometry, wherein the concentration of the adipose tissue-derived stromal stem cells in the pharmaceutical composition is at least about $5\times10^6$ cells/mL.

8. The method of claim 7, further comprising aliquoting the pharmaceutical composition into one or more doses of at least about $10\times10^6$ cells/dose.

9. The method of claim 7, further comprising aliquoting the pharmaceutical composition into one or more doses of at least about $20\times10^6$ cells/dose.

10. The method of claim 1, wherein the pharmaceutical composition further comprises an adhesive.

11. The method of claim 10, wherein the adhesive comprises a fibrin glue or gel.

12. The method of claim 1, wherein the pharmaceutical composition further comprises a therapeutic agent.

13. The method of claim 12, wherein the therapeutic agent comprises an anti-inflammatory agent, an immunosuppressive agent, a biological agent, an antibiotic, an antidiarrheal agent or a combination thereof.

14. The method of claim 7 wherein the adherent cells obtained from adipose tissue were passaged at least six times.

* * * * *

UNITED STATES PATENT AND TRADEMARK OFFICE
CERTIFICATE OF CORRECTION

PATENT NO. : 10,548,924 B2  
APPLICATION NO. : 14/017152  
DATED : February 4, 2020  
INVENTOR(S) : María Gema Fernández Miguel Page 1 of 1

It is certified that error appears in the above-identified patent and that said Letters Patent is hereby corrected as shown below:

In the Claims

In Claim 2: Line number 1, after "claim 1" please insert --,--.

In Claim 3: Line number 1, after "claim 1" please insert --,--.

In Claim 4: Line number 1, after "claim 1" please insert --,--.

In Claim 5: Line number 1, after "claim 1" please insert --,--.

In Claim 7: Line number 26, please replace "by and passaging" with "by passaging".

In Claim 14: Line number 1, after "claim 7" please insert --,--.

Signed and Sealed this  
Sixth Day of October, 2020

Andrei Iancu  
*Director of the United States Patent and Trademark Office*